United States Patent [19]

Nappholz et al.

[11] Patent Number: 5,161,527
[45] Date of Patent: Nov. 10, 1992

[54] APPARATUS AND METHOD FOR DETECTING ABNORMAL CARDIAC RHYTHMS IN DUAL CHAMBER ARRHYTHMIA CONTROL SYSTEM

[75] Inventors: Tibor A. Nappholz; Ken Koestner, both of Englewood, Colo.

[73] Assignee: Telectronics Pacing Systems, Inc., Englewood, Colo.

[21] Appl. No.: 654,930

[22] Filed: Feb. 13, 1991

[51] Int. Cl.$^5$ .............................. A61N 1/00
[52] U.S. Cl. .................. 128/419 PG; 128/419 D
[58] Field of Search ......... 128/419 PG, 419 D, 419 P

[56] References Cited

U.S. PATENT DOCUMENTS

| | | | |
|---|---|---|---|
| 3,857,398 | 12/1974 | Rubin | 128/419 D |
| 4,202,340 | 5/1980 | Langer et al. | 128/419 D |
| 4,291,699 | 9/1981 | Geddes et al. | 178/419 D |
| 4,429,697 | 2/1984 | Nappholz et al. | 128/419 PG |
| 4,475,551 | 10/1984 | Langer et al. | 128/419 D |
| 4,692,719 | 9/1987 | Whigham | 332/11 D |
| 4,766,901 | 8/1988 | Callaghan | 128/419 PG |
| 4,869,252 | 9/1989 | Gilli | 128/419 PG |
| 4,901,725 | 2/1990 | Nappholz | 128/419 PG |
| 4,940,054 | 7/1990 | Grevis et al. | 128/419 PG |
| 4,998,974 | 3/1991 | Aker | 128/419 PG |
| 5,007,422 | 4/1991 | Pless et al. | 128/419 PG |
| 5,024,222 | 6/1991 | Thacker | 128/419 PG |
| 5,027,816 | 7/1991 | Cohen | 128/419 PG |
| 4,7052,253 | 10/1987 | Nappholz et al. | 128/419 PG |

OTHER PUBLICATIONS

Fisher, et al., "Termination of Ventricular Tachycardia With Burst or Rapid Ventricular Pacing," American Journal of Cardiology, vol. 41 (Jan. 1976) p. 96.
J. D. Fisher et al., "Termination of Ventricular Tachycardia with Bursts of Rapid Ventricular Pacing," American Journal of Cardiology, vol. 41 (Jan. 1978), pp. 94-102.

Primary Examiner—Kyle L. Howell
Assistant Examiner—George Manuel
Attorney, Agent, or Firm—Gottlieb, Rackman & Reisman

[57] ABSTRACT

A rate-responsive dual-chamber antitachycardia pacer and pacing method which automatically diagnoses and supports a patient's hemodynamic status by measuring metabolic demand and sensing intracardiac electrograms to determine whether the heart is beating normally or under conditions of bradycardia, tachycardia, or fibrillation. The pacer supports the patient's metabolic demand by electrically stimulating the heart at a pacing rate driven either by the heart's sinus node or, alternatively, by the patient's metabolic demand (a metabolic demand indicator), as determined by a sensor. The pacer automatically selects between the indicated rates to determine the best pacing rate for appropriately satisfying metabolic demand at all times. The natural rate, driven by the sinus node, takes precedence over the metabolic indicator rate, provided the natural rate meets a standard determined by the metabolic demand indicator rate. The pacer detects abnormal rhythms of tachycardia and fibrillation, classifies these rhythms, and initiates an appropriate therapy accordingly, by analyzing the metabolic demand indicator and the sinus rate.

28 Claims, 10 Drawing Sheets

FIG. 12.

```
TCL = 300 ms
V-A = 70% TCL
    = 210 ms

A-V = 10 ms
    = 50 ms
    = 100 ms
    = 150 ms
```

TRAIN 1 N=4

| | A-V | | A-V | | A-V | | A-V |
|---|---|---|---|---|---|---|---|
| V-A 210 | | V-A 210 | | V-A 210 | | V-A 210 | |
| | 10 | | 10 | | 10 | | 10 |

TRAIN 2 N=4

| | A-V | | A-V | | A-V | | A-V |
|---|---|---|---|---|---|---|---|
| V-A 210 | | V-A 210 | | V-A 210 | | V-A 210 | |
| | 50 | | 50 | | 50 | | 50 |

TRAIN 3 N=4

| V-A 210 | A-V 100 | V-A 210 | A-V 100 | V-A 210 | A-V 100 | V-A 210 | A-V 100 |

TRAIN 4 N=4

| V-A 210 | A-V 150 | V-A 210 | A-V 150 | V-A 210 | A-V 150 | V-A 210 | A-V 150 |

APPARATUS AND METHOD FOR DETECTING ABNORMAL CARDIAC RHYTHMS IN DUAL CHAMBER ARRHYTHMIA CONTROL SYSTEM

TECHNICAL FIELD

This invention relates to an apparatus and method for detecting and classifying abnormal cardiac rhythms and, depending on such classification, reverting the same. More particularly, this invention relates to implantable medical devices which sense a metabolic demand indicator and derive a metabolic indicator rate parameter therefrom, sense an intrinsic rhythm from electrical activity of the heart, and analyze this rhythm in conjunction with the metabolic indicator rate parameter for the purpose of improving the detection and classification of abnormal cardiac rhythms including atrial and ventricular tachycardia, and atrial and ventricular fibrillation/flutter.

The invention promotes the efficiency of a delivered therapy in the form of electrical energy applied to cardiac tissue in both chambers of the heart in an attempt to revert tachycardia and restore a normal sinus rhythm in a dual chamber arrhythmia control system. The invention is described herein as operating in a combined implantable antitachycardia pacing, bradycardia pacing and cardioverting/defibrillating arrhythmia control system. However, the invention may also be incorporated in a device performing less than all of these functions.

BACKGROUND OF THE INVENTION

As used herein, the term tachycardia refers to any fast abnormal rhythm of the heart that is amenable to treatment by electrical discharges and specifically includes supraventricular tachycardia (SVT), atrial tachycardia (AT), atrial fibrillation and atrial flutter (AF), ventricular tachycardia (VT), and ventricular flutter and ventricular fibrillation (VF).

U.S. Pat. No. 3,857,398 to Rubin, dated Dec. 31, 1974, and entitled "Electrical Cardiac Defibrillator," describes a combined pacer/defibrillator. This device either performs a bradycardia pacing or a defibrillation function depending on the detection of a VT/VF. If a VT/VF is detected, the device is switched to the defibrillating mode. After a period of time to charge the capacitor, a defibrillation shock is delivered to the patient.

Improvements on this device were contained in a multiprogrammable, telemetric, implantable defibrillator which is disclosed in copending patent application Ser. No. 239,624 to Gilli et al., filed Sep. 1, 1988, and entitled "Reconfirmation Prior to Shock in Implantable Defibrillator". The Gilli et al. device contains a bradycardia support system as well as a high energy shock system to revert ventricular tachycardias to normal sinus rhythm. On reconfirmation of the presence of a tachycardia, a shock is delivered to the patient at a predetermined time or when the desired energy level is reached.

As cardioversion or defibrillation shocks can be very unpleasant to a patient, especially when delivered frequently, it became necessary therefore to provide a device which included antitachycardia pacing therapy along with bradycardia support pacing therapy and defibrillation or cardioversion therapy, so that the implanted device could automatically provide the necessary therapy from a range of therapies offered by the device. Hence a further development in the field of combined implantable devices is described in U.S. Pat. No. 4,940,054, to Grevis and Gilli, dated Jul. 10, 1990, and entitled "Apparatus and Method for Controlling Multiple Sensitivities in Arrhythmia Control Systems Including Post Therapy Pacing Delay". This device is a microcomputer based arrhythmia control system which is programmable by means of a telemetric link. The device provides single chamber bradycardia support pacing, antitachycardia pacing, and cardioversion or defibrillation shocks for restoring normal sinus rhythm to a patient.

Additionally, various specific developments have been made in the field of tachycardia control pacers. Tachycardia is a condition in which the heart beats very rapidly, with a ventricular rate higher than 100 beats per minute (bpm) and typically above 150 bpm, and an atrial rate as high as 400 bpm. There are several different pacing modalities which have been suggested for the termination of tachycardia. The underlying principle in all of them is that if a pacer stimulates the heart at least once shortly after a heartbeat, before the next naturally occurring heartbeat at the rapid rate, the heart may successfully revert to normal sinus rhythm. Tachycardia is often the result of electrical feedback within the heart. A natural beat results in the feedback of an electrical stimulus which prematurely triggers another beat. By interposing a stimulated heartbeat, the stability of the feedback loop is disrupted.

U.S. Pat. No. 4,202,340, to Langer et al., dated May 13, 1980, and entitled "Method and Apparatus for Monitoring Heart Activity, Detecting Abnormalities, and Cardioverting a Malfunctioning Heart," describes an antitachycardia pacing system which detects VT/VF by deriving a probability density function from the analysis of the amplitudes of intracardiac signals. This antitachycardia pacing system is subject to errors in the delivery of therapy due to the erratic and unpredictable nature of intracardiac signals.

The system disclosed in U.S. Pat. No. 4,475,551, to Langer et al., dated Oct. 9, 1984, and entitled "Arrhythmia Detection and Defibrillation System and Method," illustrates arrhythmia detection in which the device first analyzes the probability density function to ascertain abnormal cardiac rhythms such as fibrillation, high rate tachycardias, and low rate tachycardias. Upon the discovery of such rhythms, the device senses heart rate so as to distinguish fibrillation and high rate tachycardia from low rate tachycardia. This device employs a predetermined threshold value for the rate which distinguishes such arrhythmia events.

U.S. Pat. No. 4,291,699, to Geddes, dated Sep. 29, 1981, and entitled "Method and Apparatus for Automatically Detecting and Treating Ventricular Fibrillation," characterizes a defibrillator which senses both the electrical and mechanical activity of the heart to detect fibrillation. This device measures the mechanical pumping action of the heart by detecting changes in electrical impedance between a pair of electrodes implanted within one of the ventricles of the heart.

Dual chamber heart pacers have been developed in order to generate sequential atrial and ventricular pacing pulses which closely match the physiological requirements of the patient. A conventional dual chamber heart pacer as disclosed in U.S. Pat. No. 4,429,697 to Nappholz et al. dated Feb. 7, 1984, and entitled "Dual Chamber Heart Pacer With Improved Ventricular Rate Control," includes atrial beat sensing and pulse generating circuits along with ventricular beat sensing and pulse generating circuits. It is known that the detection of a ventricular beat or the generation of a ventricular pacing pulse initiates the timing of an interval known as the V-A delay. If an atrial beat is not sensed prior to expiration of the V-A delay interval, then an atrial pacing pulse is generated. Following the generation of an atrial pacing pulse, or a sensed atrial beat, an interval known as the A-V delay is timed. If a ventricular beat is not sensed prior to the expiration of the A-V delay interval, then a ventricular pacing pulse is generated. With the generation of a ventricular pacing pulse, or the sensing of a ventricular beat, the V-A delay timing starts again. This patent describes how the V-A delay timing interval may be divided into three parts; the atrial refractory period, the Wenckeback timing window, and the P-wave synchrony timing window. It outlines the importance of controlling the ventricular rate in comparison with the atrial rate in order to maintain synchrony between the atrium and the ventricle. The patent does not however address the issue of antitachycardia pacing therapy.

Physiological pacers adapt pacing rate and timing to the patient's needs based on one of two general schemes: dual-chamber pacing in which intrinsic atrial activity triggers ventricular pacing, and pacing (single-chamber or dual-chamber) at a ventricular rate related to metabolic demand which is sensed in some manner. Each method of rate adaptation has inherent advantages and disadvantages which a physician must consider in determining the best method for pacing within a diverse patient population.

Dual-chamber pacemakers perform rate adaptation by means of atrial synchronous ventricular pacing where sensing of a natural atrial pulse, called a P wave, activates the process leading to ventricular demand pacing by starting the timing period called the A-V interval. During the A-V interval, the ventricular sense amplifier is capable of sensing a naturally occurring ventricular contraction, or R wave. If the pacer senses an R wave during the A-V interval, a second time period called the V-A interval is immediately started, at the end of which an atrial pulse is generated. If the A-V interval times out before R wave sensing, however, the pacemaker stimulates the ventricle and the V-A interval begins at the end of the A-V interval. This operating mode, characterized by pacing, sensing, and inhibition in both chambers is termed a DDD mode. Atrial synchronous ventricular pacing is best for patients and conditions in which the sino-atrial node is normally responsive to metabolic demands since intrinsic stimulation by the sinus node appropriately controls cardiac rate. Pacing in a dual-chamber manner promotes efficient cardiac output by pacing at a natural rate and by maintaining physiological A-V synchrony. DDD pacing is ineffective where an electrically unstable atrium produces frequent extra-systoles, creating intermittent atrial flutter or fibrillation.

Metabolic demand pacemakers, on the other hand, perform rate adaptation using various sensors within the body to measure a parameter related to metabolic demand and to determine a desired pacing rate independent of atrial activity. Recent pacemaker technological advances include a number of accurate physiological sensor mechanisms for determining pacing rate in response to metabolic needs of the body. These metabolic demand pacemakers have clinically proven themselves to properly support the patient's needs. The pacemaker measures a metabolic sensor parameter and, from the parameter, determines a metabolic indicator rate (MIR). In one example of a metabolic demand indicator scheme, U.S. Pat. No. 4,901,725, dated Feb. 20, 1990 to Nappholz et al., entitled "Minute Volume Rate-Responsive Pacemaker," changes in minute ventilation, measured using transthoracic impedance, correlate positively to heart rate. Updating cardiac rate relative to the minute ventilation measurement increases pacing rate in a stable but rapid manner, proportional to the level of the workload. Because such pacers do not directly trigger ventricular pacing upon atrial sensing, it follows that these pacemakers do not drive the ventricle in response to unstable upper atrial rate behavior or induce pacemaker mediated tachycardia. However, these pacers do not provide the hemodynamic efficiency inherent in A-V synchronous pacing; in many metabolic pacemakers, the sensor mechanism responds to changing metabolic demand more slowly than a system driven by the sinus node. Also, because a metabolic sensor measures a parameter only secondarily related to cardiac function, extrinsic influences on the sensor may change the heart rate inappropriately.

Prior art single chamber antitachycardia pacing devices which provide antitachycardia pacing bursts to either the atrium or the ventricle have shortcomings in that they lack the required synchrony between the atrium and the ventricle. This reduces the percentage of successful reversions, especially in the case of ventricular antitachycardia pacing. Although such pacing may revert an arrhythmia, at the same time however, it increases the risk of adversely affecting the patient by means of a decrease in arterial pressure due to the rapid pacing. Possibly, as a result of the hemodynamic compromise or lowered hemodynamic status of the myocardium during the arrhythmia and pacing which reduces electrical conduction in the heart, there is a high risk of a ventricular tachycardia accelerating to a faster ventricular tachycardia and even to a ventricular fibrillation. This has been shown in an article by Fisher et al. entitled "Termination of Ventricular Tachycardia with Burst or Rapid Ventricular Pacing", American Journal of Cardiology, Vol. 41 (January, 1978), page 96. Not only does this present a potentially hazardous situation to the patient, but it also makes it more difficult for the device to revert the patient. Reversion would necessarily demand more energy of the device and perhaps even cardioversion or defibrillation therapy which is not available in many pacing devices. Furthermore, prior art devices are very limited in the provision of individualized therapy to the patient by patient dependent parameters such as the A-V delay.

Many antitachycardia pacing therapy devices at present include defibrillation support within the device in order to provide adequate safety to a patient. It is highly advantageous to prevent the development of VT's or atrial fibrillations, or to terminate them quickly if they appear, rather than allowing the arrhythmia to develop to such an extent that a defibrillation shock is necessary.

The use of antitachycardia pacing therapy in conjunction with a dual chamber pacing device is disclosed in the copending application of Norma L. Gilli, Ser. No. 462,499, filed Jan. 5, 1990, and entitled "Apparatus and Method for Antitachycardia Pacing in Dual Chamber Arrhythmia Control System", which application is assigned to the assignee of the present invention. In the Gilli application upon detection of the presence of a tachycardia, the tachycardia cycle length (TCL) is measured and a V-A interval less than or equal to the TCL is determined, along with an initial value A-V interval. Stimulation pulses are then delivered until the expiration of a given number (N) V-A intervals and N A-V intervals to complete a first train of pulses. A series of a given number (M) of trains of pulses similar to the first train of pulses is delivered, and the A-V delay interval value is varied from the initial value thereof at least once prior to the completion of the series of M trains of pulses. Monitoring of intrinsic QRS complexes between pulse trains is performed. If the tachyarrhythmia is deemed to be accelerating, one of cardioversion or defibrillation is employed. The present invention is an improvement over said Gilli application with respect to the manner of detecting tachyarrhythmias and the manner of setting the A-V interval during the application of antitachycardia pacing therapy.

SUMMARY OF THE INVENTION

In accordance with the principles of our invention, the antitachycardia pacer derives a metabolic indicator rate using at least one metabolic indicator sensor and uses this parameter not only to define an appropriate rate for bradycardia pacing, but also to define the limits distinguishing physiological from pathological intrinsic cardiac rhythms. A-V synchronous pacing, driven naturally by the sinus node to yield normal, synchronized atrial and ventricular contractions, is the most efficient manner of operation to optimize cardiac output. In the diseased heart, however, atrial tachycardia, bradycardia, unstable physiology or other pathological conditions may exist. The metabolic indicator rate parameter derivation operates independently from sinus node and atrial activity, providing reliable determination of metabolic demand and the pacing rate required to satisfy that demand. A physiological sensor or combination of sensors in the DDDR (DDD with rate response) system of the present invention sets limits which indicate when sinus node and atrial physiology are not performing reliably. This allows the pacemaker to detect pathological behavior and respond in a manner to revert the condition, maintaining a stable and appropriate pacing rate despite occurrences of atrial instability The pacer first determines the metabolic indicator rate and uses this rate to vary both the overall pacing rate and a maximum atrial tracking rate (the highest atrial rate which maintains A-V synchrony). By setting the overall pacing rate according to the metabolic indicator rate, the pacemaker determines the lower limit of the cardiac rate when atrial activity is slow or absent. In addition, using the metabolic indicator rate to determine the maximum atrial tracking rate allows the pacer to respond to exercise in a manner which maintains A-V synchrony all the way up to a programmed maximum rate without dropping ventricular activity in response to elevated rate atrial heartbeats. When a patient exercises, the metabolic indicator rate increases, elevating the maximum atrial tracking rate. This, in turn, means that as the sinus rate increases with exercise, it is less likely to exceed the maximum atrial tracking rate and the pacer can maintain stimulating in the A-V synchronous mode.

In a sense, the pacer of our invention controls pacing rate in an anomalous manner. The metabolic indicator rate has the ultimate control. By varying the maximum atrial tracking rate based on the metabolic indicator rate, the pacer determines whether the sinus rate is physiological or pathological. Despite the fact that the metabolic indicator rate is given this ultimate control, however, it is not treated as the best indicator of metabolic needs. As long as the metabolic indicator rate sets the maximum allowed atrial tracking rate greater than the intrinsic atrial rate, the pacing rate is left under the control of the sinus node and atrial conduction physiology. This method of operation is the same as traditional DDD pacing wherein an atrial beat triggers the A-V delay. The DDDR system improves on DDD pacing since the metabolic indicator rate automatically and continuously updates both the duration of the A-V delay and the cardiac cycle length to reflect the metabolic needs of the body and cardiovascular hemodynamics. The metabolic indicator rate takes control only when the intrinsic atrial rate is too low or too high. If the intrinsic atrial rate is too low, the pacer stimulates the atrium at the metabolic indicator rate and, if it does not sense natural ventricular depolarization during the A-V delay interval, stimulates the ventricle after the A-V delay interval. The metabolic indicator rate also takes control of antitachycardia pacing, upon establishing that the sinus rate is too high. The pacer thus gives preference to the sinus rate even though the ultimate arbiter between the rates is the metabolic indicator rate.

It is an object of the present invention to provide an improved, rate-responsive, dual chamber antitachycardia pacing device for the reversion of tachycardias.

It is a further object of the present invention to provide an improved method of antitachycardia pacing in a rate-responsive dual chamber pacing device.

It is another object of the present invention to provide an improved rate-responsive dual chamber antitachycardia pacing device and method which accommodates atrioventricular synchrony, from low resting rates to high exercise rates, while providing antitachycardia and defibrillation therapy support in response to pathological rhythms.

It is an additional object of the invention to provide improved detection and classification of abnormal and pathological cardiac rhythms for the purpose of providing improved antitachycardia pacing therapy in an automatic implantable device.

It is a further object of the invention to provide, in a dual chamber antitachycardia pacing device and method, for improved maintenance of synchrony between the atrium and the ventricle during elevated metabolic demand conditions to minimize the possible emergence of arrhythmia events.

It is a still further object of the invention to provide a rate-responsive dual chamber antitachycardia pacing device and method having an improved capability for distinguishing physiological from pathological cardiac rhythms.

It is an additional object of the invention to provide an improved rate-responsive dual chamber arrhythmia control system in which parameters such as the A-V delay may be programmed as a percentage of a metabolic indicator cycle length.

It is another object of the invention to provide arrhythmia detection parameters based on a combination of metabolic indicator sensors, including a fast-acting sensor for rapid response and a slower sensor for stability of control, which define a pathological condition. Fast-acting detectors include sensors of intracardiac evoked potential amplitude, changes in intracardiac pressure, activity, or changes in respiratory minute volume. Stable slower detectors include sensors of respiratory minute volume, QT interval, and temperature.

It is yet another object of the invention to provide an improved arrhythmia detection device and method which utilize sensing both of evoked potential amplitude for fast response, and respiratory minute volume for stability.

In accordance with the principles of the present invention, the rate-responsive dual chamber antitachycardia pacer and pacing method automatically diagnoses and supports a patient's hemodynamic status by measuring metabolic demand and sensing intracardiac electrograms to determine whether the heart is beating normally or under conditions of exercise, bradycardia, tachycardia, or fibrillation. If the heart is functioning normally or in bradycardia or exercise, the pacer supports the patient's metabolic demand by electrically stimulating the heart at a pacing rate driven by the heart's sinus node or, alternatively, by a sensor adapted to determine the patient's metabolic demand (a metabolic demand indicator). The pacer automatically selects between the indicated rates to determine the best pacing rate for appropriately satisfying metabolic demand at all times. The natural rate, driven by the sinus node, takes precedence over the metabolic indicator rate provided the natural rate meets a standard determined by the metabolic demand indicator rate. The pacer detects abnormal rhythms of tachycardia and fibrillation, classifies these rhythms, and initiates an appropriate therapy accordingly, by analyzing the metabolic demand indicator and the sinus rate.

The pacer upper rate response mechanism allows atrioventricular synchrony at natural sinus rates ranging from low rates to high exercise rates, even up to the programmed maximum rate, while providing antitachycardia and defibrillation therapy support in response to pathological rhythms.

BRIEF DESCRIPTION OF THE DRAWINGS

Further objects, features and advantages of the invention will become apparent upon consideration of the following description, taken in conjunction with the accompanying drawings, in which:

FIG. 12 illustrates an embodiment of a dual chamber antitachycardia pacing algorithm according to the invention;

DETAILED DESCRIPTION OF THE INVENTION

Figure 1:
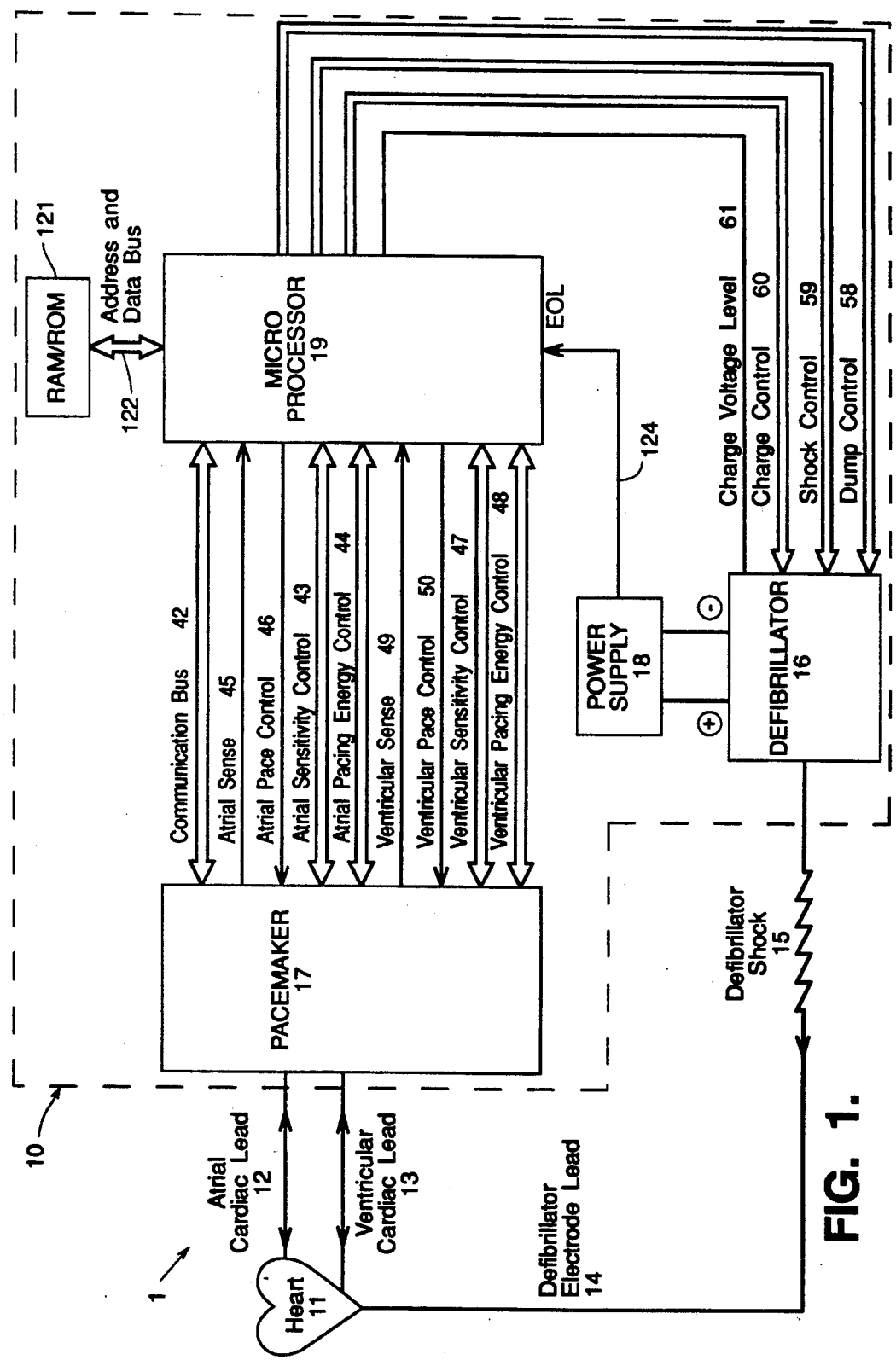
FIG. 1 is a block diagram of an implanted, rate-responsive, dual chamber arrhythmia control system (ACS) in accordance with the present invention.

Referring to FIG. 1, there is depicted a block diagram of an arrhythmia control system 1. System 1 is designed to be implantable in a patient and includes a pulse module 10 and appropriate leads for connecting module 10 to a patient's heart 11. More particularly, system 1 will generally include an atrial cardiac lead 12 extending to the atrium of the patient's heart for the administration of therapy to the atrium, and a ventricular cardiac lead 13 extending to the ventricle of the patient's heart for the administration of therapy to the ventricle. System 1 generally also includes a pacemaker 17 for the detection of analog signals representing cardiac electrical activity and for the delivery of pacing pulses to the heart; a microprocessor 19 which, in response to various inputs received from the pacemaker 17 as well as from a defibrillator 16, performs various operations so as to generate different control and data outputs to both pacemaker 17 and defibrillator 16; and a power supply 18 for the provision of a reliable voltage level to pacemaker 17, microprocessor 19 and defibrillator 16 by suitable electrical conductors (not shown). Defibrillator 16 produces a high voltage to charge its capacitors and then discharges them in response to control signals from microprocessor 19. A defibrillator electrode lead 14 transfers the energy of a defibrillator shock 15 from the implanted pulse module 10 to the heart 11.

Microprocessor 19 is connected to a random access memory/read only memory (RAM/ROM) unit 121 by an address and data bus 122. An end-of-life (EOL) signal line 124 is used to provide, to microprocessor 19, a logic signal indicative of the approach of battery failure in power supply 18. As more fully described below, microprocessor 19 and pacemaker 17 are connected by a communication bus 42, an atrial sense line 45, an atrial pace control line 46, an atrial sensitivity control bus 43, an atrial pace energy control bus 44, a ventricular sense line 49, a ventricular pace control line 50, a ventricular sensitivity control bus 47, and a ventricular pace energy control bus 48. As also more fully described below, microprocessor 19 is connected to defibrillator 16 by a charge voltage level line 61, a charge control bus 60, a shock control bus 59, and a dump control bus 58.

Figure 2:
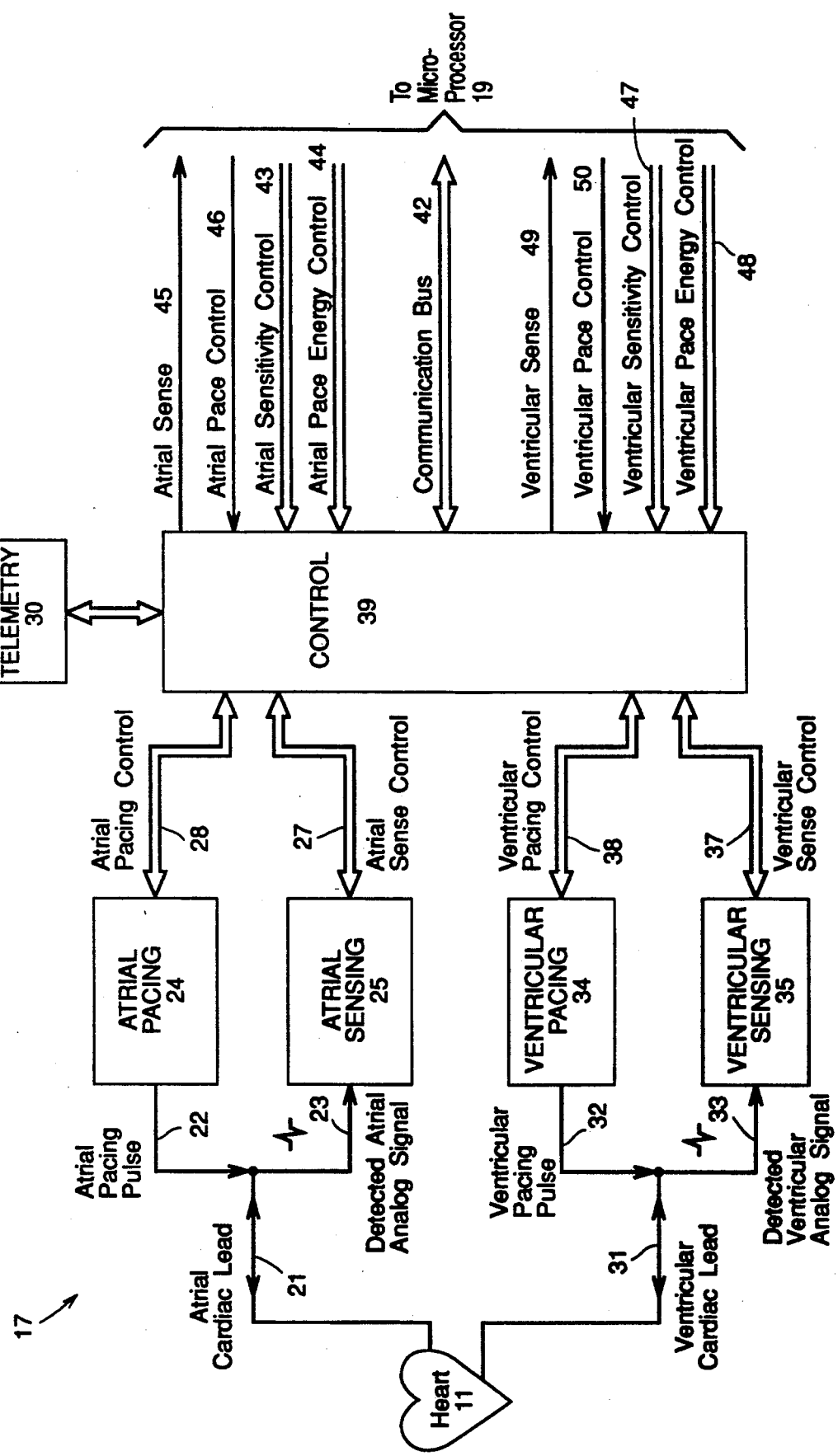
FIG. 2 is a block diagram of a pacemaker utilized in the system of FIG. 1.

Referring to FIG. 2, pacemaker 17 comprises circuitry for atrial pacing 24, ventricular pacing 34, atrial sensing 25, ventricular sensing 35, and telemetry 30. In addition, pacemaker 17 includes a control block 39 which includes an interface to microprocessor 19.

In operation, sensing circuits 25 and 35 detect respective atrial and ventricular analog signals 23 and 33 from the heart 11 and convert the detected signals to digital signals. In addition, the sensing circuits 25 and 35 receive an input atrial sense control 27 and an input ventricular sense control 37, respectively, from the control block 39 which determines the sensitivity applied to the detection circuit. As more fully described below, a change in this sensitivity affects the voltage deviation required at the sensing electrode for a sense to be registered. The operation of the logic which changes the sensitivity is described in greater detail in the aforesaid U.S. Pat. No. 4,940,054 of Grevis and Gilli, which description is incorporated herein by reference.

Atrial pacing circuit 24 receives from control block 39, via an atrial pacing control bus 28, an atrial pace control input and an atrial pacing energy control input. Similarly, ventricular pacing circuit 34 receives from control block 39, via a ventricular pacing control bus 38, a ventricular pace control input and a ventricular pacing energy control input. The atrial and ventricular pace control inputs determine the respective types of atrial and ventricular pacing to occur, while the atrial and ventricular pacing energy control inputs determine the respective magnitudes of the pulse energy. The operation of the logic which changes the pulse energy is described in greater detail in U.S. Pat. No. 4,869,252 to Norma Louise Gilli, issued Sep. 26, 1989, and entitled "Apparatus And Method For Controlling Pulse Energy In Antitachyarrhythmia And Bradycardia Pacing Devices," which description is incorporated herein by reference.

Telemetry circuit 30 provides a bidirectional link between control block 39 of pacemaker 17 and an external device such as a programmer. It allows data such as the operating parameters to be read from or altered in the implanted module 10.

Figure 3:
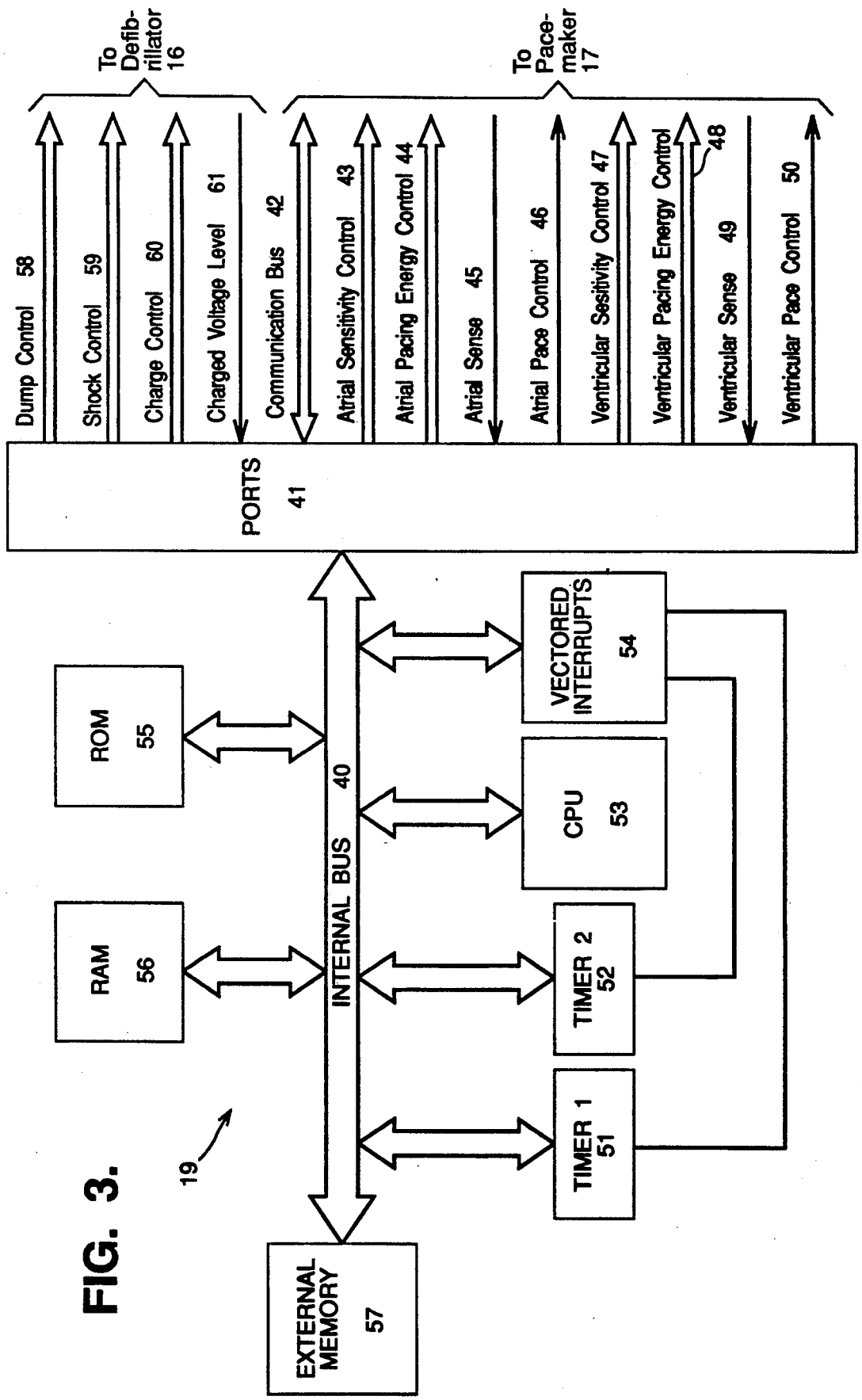
FIG. 3 is a block diagram of a microprocessor utilized in the system of FIG. 1.

Referring to FIG. 3, microprocessor 19 comprises two 16-bit timers 51 and 52, a CPU 53, a vectored interrupts block 54, a ROM 55, a RAM 56, an external memory 57, a ports block 41 and an internal communications bus 40. RAM 56 acts as a scratch pad and active memory during execution of the various programs stored in ROM 55 and used by microprocessor 19. These programs include system supervisory programs, detection algorithms for detecting and confirming various arrhythmias, and programming for implementing the logic flow diagram of FIG. 13, as well as storage programs for storing, in external memory 57, data concerning the functioning of module 10 and the electrogram provided by ventricular cardiac lead 13 (FIG. 1). Timers 51 and 52, and associated control software, implement some timing functions required by microprocessor 19 without resort entirely to software, thus reducing computational loads on and power dissipation by CPU 53.

Signals received from telemetry circuit 30 (FIG. 2) permit an external programmer (not shown) to change the operating parameters of pacemaker 17 by supplying appropriate signals to control block 39. Communications bus 42 serves to provide signals indicative of such control to microprocessor 19. Thus, it is also possible for an external programmer to control operation of defibrillator 16 by means of signals provided to microprocessor 19.

Appropriate telemetry commands may cause telemetry circuit 30 to transmit data to the external programmer. Data stored is read out, by microprocessor 19, on to communications bus 42, through control block 39 in pacemaker 17, and into telemetry circuit 30 for transmission to the external programmer by a transmitter in telemetry circuit 30.

Microprocessor 19 receives various status and/or control inputs from pacemaker 17 and defibrillator 16, such as the sense signals on sense lines 45 and 49. It performs operations, such as arrhythmia detection, and produces outputs, such as the atrial pace control on line 46 and the ventricular pace control on line 50, which determine the type of pacing that is to take place. Other control outputs generated by microprocessor 19 include the atrial and ventricular pacing energy controls on buses 44 and 48, respectively, which determine the magnitude of the pulse energy, the shock control on bus 59 which signals that a shock is to be delivered to the patient, the dump control on bus 58 which indicates that a shock is to be dumped at an internal load within the defibrillator, the charge control on bus 60 which determines the voltage level of the shock to be delivered, and the atrial and ventricular sensitivity controls on buses 43 and 47, respectively, which determine the sensitivity settings of the sensing circuits. Charge voltage level line 61 provides a digital signal representative of charge voltage from an analog-to-digital converter within defibrillator 16, thus providing a feedback loop which assures that a shock of proper energy level is delivered by defibrillator 16.

Figure 4:
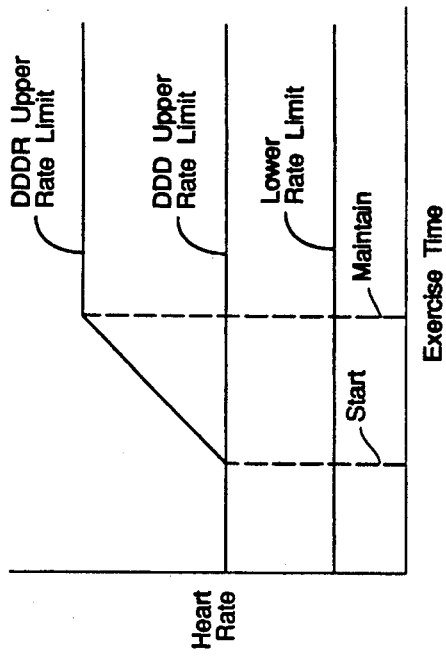
FIG. 4 is a graph of heart rate vs. stress due to exercise, illustrating how the pacemaker of the present invention determines maximum atrial tracking rate from metabolic indicator rate while the patient is exercising.

FIG. 4 illustrates a typical relationship between a metabolic indicator rate and a maximum atrial tracking rate.

There is a considerable body of prior art in dual-chamber pacers which automatically select a mode of operation, on a cycle by cycle basis, by enabling or disabling atrial and ventricular pacing and sensing. The use of an external programmer to communicate with an implanted pacemaker is also well known. U.S. Pat. No. 4,766,901, to Callaghan, dated Aug. 30, 1988, and entitled "Rate Responsive Pacing System Using the Integrated Evoked Potential," refers to the operation of a rate-responsive pacing system using an integrated evoked potential for a metabolic demand pacing rate indicator. U.S. Pat. No. 4,702,253 to Nappholz et al. dated Oct. 27, 1987, and entitled "Metabolic-Demand Pacemaker and Method of Using the Same to Determine Minute Volume," discloses a rate-responsive pacer describing a second metabolic demand pacing rate indicator, respiratory minute volume, as the rate control parameter. U.S. Pat. No. 4,692,719 to Whigham, dated Sep. 8, 1987, and entitled "Combined Pacemaker Delta Modulator and Bandpass Filter," describes electronic circuitry capable of performing electrocardiogram sensing for analyzing intrinsic and evoked potential cardiac signals. Improved pacers are disclosed in Callaghan et Al. Application Ser. No. 173,573 entitled "Rate-Responsive Pacemaker with Closed-Loop Control", filed on Mar. 25, 1988, and in the aforesaid U.S. Pat. No. 4,901,725 to Nappholz et al. The above-mentioned patents and applications are hereby incorporated by reference.

A metabolic sensing system suitable for the present invention could be made up of one or more of various sensing mechanisms, including but not limited to minute volume, depolarization gradient of the evoked potential, QT-interval, oxygen saturation, pH, central venous blood temperature, right ventricular pressure, stroke volume, systolic time intervals, respiration rate, and ultrasound. The method and apparatus of our invention will work with any metabolic indicator system able to reliably relate the sensor parameter to metabolic demand pacing rate. Preferred embodiments include either minute volume, integrated evoked potential, or both in a dual sensor system. Telemetry between an external programmer and the pacemaker may activate or deactivate a sensor system or control the influence of both sensors in a dual sensor system. The combination of minute volume and evoked potential sensor systems does not require additional sensing leads over the number required for a DDD system alone.

The antitachycardia pacer of the present invention first determines the metabolic indicator rate from measurements of respiratory minute volume (MIRmv) in the manner described in the aforesaid Nappholz et. al. U.S. Pat. No. 4,901,725. The antitachycardia pacer also derives a second metabolic indicator rate from integrated evoked potential measurements (MIRep), according to the disclosure of the aforementioned Callaghan U.S. Pat. No. 4,766,901. The pacer limits MIRep and MIRmv to predetermined maximum values, with MIRep limited to a lower rate than MIRmv. The pacer then compares current MIRmv and MIRep values and sets the metabolic indicator rate (MIR) to the maximum of the two, for each cardiac cycle, and derives operational rates or intervals from MIR. In general, it is desirable that multiple MIR sensors be employed and that they function independently, with one MIR sensor responding quickly to increases in metabolic demand, and a second MIR sensor responding in a slower, more stable manner. In the preferred embodiment of the invention, MIRep is the parameter of rapid response and MITmv offers stability.

For a given implementation, the metabolic indicator rate-determining method may supply the pacer with the metabolic indicator rate or its reciprocal, the metabolic indicator rate interval (MIRI). From either of these MIR parameter values, the pacer determines necessary rates or intervals. The pacer uses the MIR parameter to determine (a) the minimum cardiac pacing rate, (b) the maximum atrial tracking rate, (c) various tachycardia cycle length (TCL) limits, and (d) A-V delay for maintaining synchrony in the heart chambers.

(a) The minimum cardiac pacing rate is the overall DDDR pacing rate, the lower limit of the cardiac rate when atrial activity is slow or absent. In the illustrative embodiment of the invention, the pacer sets the minimum cardiac pacing rate equal to the MIR.

(b) The maximum atrial tracking rate is the highest intrinsic atrial rate for which the ventricle is paced in synchrony with natural atrial activity. The pacer sets the maximum atrial tracking rate to a rate proportional to and higher than the MIR to allow sinus node tracking during exercise or stress. The relationship for determining maximum atrial tracking rate from the metabolic indicator rate is based on a clinical evaluation of the particular metabolic indicator method and how the derived MIR relates to the upper limit on pacing rate for an exercising patient. By basing the maximum atrial tracking rate on the MIR, when the patient exercises the metabolic indicator rate increases and this elevates the maximum atrial tracking rate. In turn, as the sinus rate increases with exercise, it is less likely to exceed the maximum atrial tracking rate and the pacemaker can remain in the A-V synchronous mode.

Referring to FIG. 4, wherein A-V synchrony exists at all times that the heart rate, as indicated by the metabolic indicator rate, is either below or equal to the maximum atrial tracking rate, the pacer maintains A-V synchrony from low intrinsic atrial rates all the way to the programmed maximum atrial tracking rate during exercise so long as the intrinsic rate does not exceed the maximum atrial tracking rate.

Figure 5:
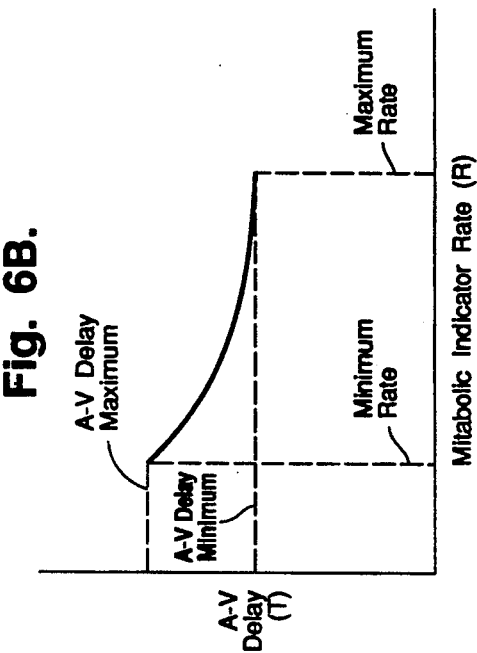
FIG. 5 is a graph of heart rate vs. stress due to exercise, comparing the exercise response of the pacemaker of the present invention to the exercise response of a prior art DDD pacemaker, and showing the improvement in atrial tracking ability of the pacemaker of the present invention.

Referring to FIG. 5, the exercise response of a standard DDD pacer is compared with that of the present DDDR pacer invention. Because the DDD upper rate limit does not change in response to exercise, a DDD pacer maintains A-V synchrony only to a level considered safe for a resting patient. During exercise, the DDD pacer starts its upper rate response at a much lower intrinsic atrial rate, defeating A-V synchrony when its efficiency is most needed.

(c) Tachycardia cycle length (TCL) limits are employed by an arrhythmia detector to classify abnormal cardiac rhythms and, thereby, to determine the therapy performed by the pacer. The arrhythmia detector senses cardiac events and updates an X out of Y detector (the X/Y detector) to distinguish different types of cardiac rhythms The X/Y detector measures the time interval between consecutive cardiac events and inserts this interval into a memory containing a history of such intervals. The detector compares at least one element of this history of intervals with a predetermined detection interval. The X/Y detector analyzes this history according to a preset detection criterion, X out of Y (for example, 8 out of 10 intervals). The cardiac rhythm meets this detection criterion when at least X of the Y most recent intervals are shorter than, or equal to, the detection interval.

The arrhythmia detector is comprised of detectors of three types of arrhythmia events, listed in their order of priority: fibrillation, tachycardia, and the onset of tachycardia. If the history of cardiac events meets the criteria for more than one type of arrhythmia, the device classifies the event according to the higher priority.

The fibrillation detector categorizes a cardiac rhythm as fibrillation, a tachycardia with a very short interval, when the cardiac rate is sufficiently fast and sustained that it meets an X/Y detector criterion measured by comparing the history of cardiac intervals with a Fibrillation Detection Interval (FDI) limit value of about 250 milliseconds.

The tachycardia detector classifies a cardiac rhythm as a tachycardia when the cardiac rate is slower than the fibrillation rate but faster than a nontachycardia rate for a preponderance of cardiac cycles so that the rate exceeds the X/Y detector criterion formed by a comparison of the history of cardiac intervals to a Tachycardia Detection Interval (TDI) limit. The TDI limit is set within the range of 300 to 600 milliseconds, according to the current value of the metabolic indicator rate (MRI) and interval (MIRI), as is described hereinafter. This defines tachycardia rates from 200 to 100 bpm, respectively. The TDI is always longer than the FDI.

A sudden and sustained decrease in interval duration activates the tachycardia onset detector, which examines the cardiac interval history to discern a sudden decrease in interval length while performing X/Y detection. In this X/Y detection step, the pacer compares the interval history with an Onset Detection Interval (ODI) limit, which the pacemaker automatically sets as a function of MIRI, to ascertain whether a decrease in interval length is sustained. The ODI limit, like the TDI limit, ranges from 300 to 600 ms. The amount of decrease in interval length (Delta) and the number of cardiac cycles within which the decrease occurs have predetermined values. In the preferred embodiment of the invention the ODI calculates the average interval in the interval history using one or more cardiac interval samples preceding the Y intervals defined by the X/Y detector. This provides a reference value against which the tachycardia onset detector measures changes of interval. Upon meeting the change in interval criterion, the X/Y detector then ascertains that all Y intervals remain at least Delta shorter than the calculated average interval and that at least X out of Y intervals are also shorter than or equal to ODI.

The antitachycardia pacer confirms the presence of tachyarrhythmia before delivering each ATP train or cardioversion/defibrillation shock. Tachyarrhythmia confirmation employs an X/Y detector, as previously described. Each confirmation test requires redetermination of the tachyarrhythmia confirmation interval (TCI) for comparison with the current interval by the X/Y detector. The operational value of the TCI depends on the identity of the detector which discerned the tachyarrhythmia. Initiation by the tachycardia onset detector causes the device to calculate TCI dynamically, setting TCI to the average interval before onset less a fraction of Delta (for example, one-half). Otherwise, the device sets TCI equal to TDI. In either case, TCI is limited to values between ODI and TDI.

Upon confirming the presence of tachyarrhythmia but prior to delivering therapy, the device classifies the tachyarrhythmia to determine the appropriate therapy. Classification is based on analysis using the X/Y detector in conjunction with two intervals of predetermined duration, the Minimum Tachycardia Cycle Length for ATP (TCLminATP) and the Maximum Tachycardia Cycle Length for Defibrillation (TCLmaxD). TCLminATP represents the tachycardia cycle length below which intervals are too short for antitachycardia pacing to be effective TCLmaxD represents the tachycardia cycle length below which the patient is hemodynamically compromised by the tachyarrhythmia and, therefore, requires shock therapy Note that TCLmaxD must always be greater than TCLminATP The predetermined values cannot define a range of intervals which are too short for antitachycardia pacing but too long for shock therapy. The range of allowable values for TCLminATP and TCLmaxD is illustrated by the lower and upper broken lines in FIG. 11.

Figure 11:
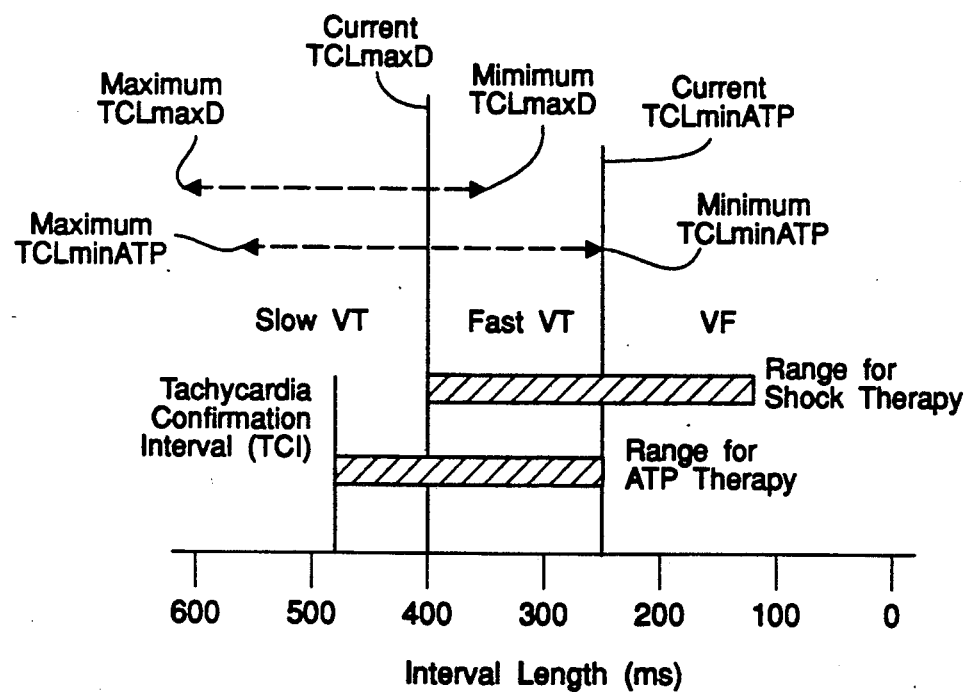
FIG. 11 is a graphic representation of tachycardia classifications as a function of interval length.

Referring to FIG. 11, these intervals allow tachyarrhythmia classification into three types on the basis of the TCL Slow VT occurs when the tachycardia cycle length is longer than the current TCLmaxD The device does not perform antitachycardia pacing in this instance. Fast VT arises when the tachycardia cycle length is longer than the current TCLminATP and shorter than or equal to the current TCLmaxD The device initiates antitachycardia pacing for cycle lengths within this range, and also uses shock therapy if the abnormal rhythm is not reverted by such therapy. VF occurs when the cycle length is shorter than or equal to the current TCLminATP. For such cycle lengths, the device only employs shock therapy.

The pacer derives the metabolic indicator rate parameter and establishes the operational pacing rates; also, during each cycle it senses natural atrial activity for the purpose of measuring the intrinsic atrial rate. The pacer compares the intrinsic atrial rate to the maximum atrial tracking rate to determine the pacing rate and type of therapy for that, and possibly other, cardiac cycles.

Figure 7A:
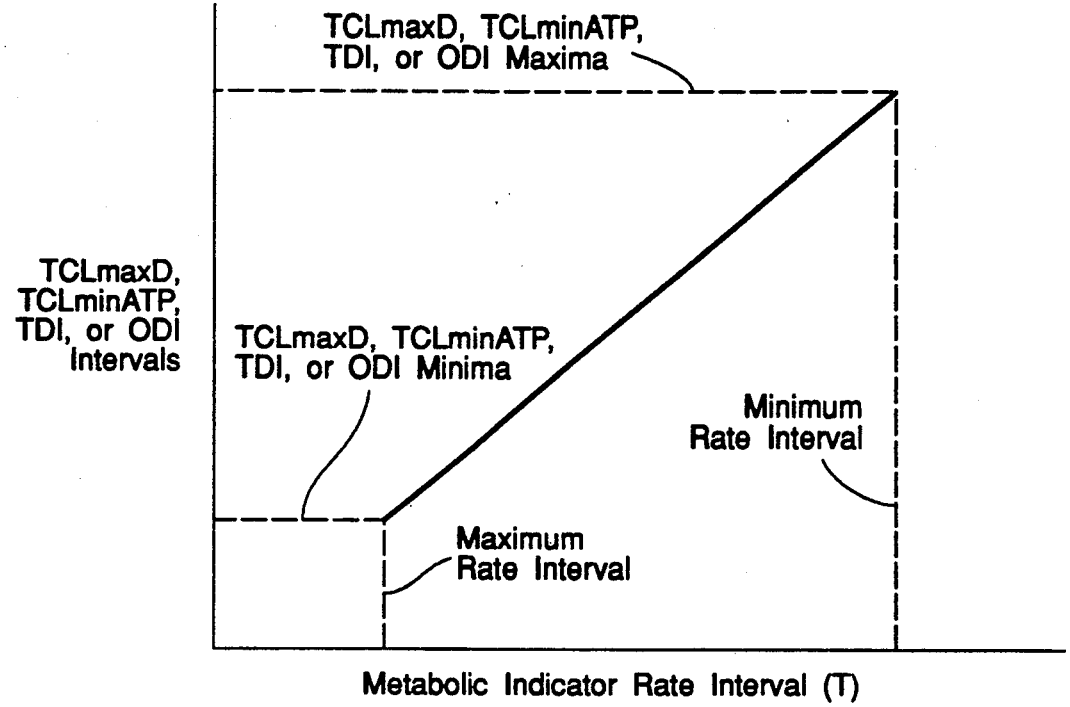
FIGS. 7A and 7B set forth graphic representations of the mechanism for automatically determining a rate adaptable maximum atrial tracking rate interval from the metabolic indicator rate, in terms of cardiac cycle time (FIG. 7A) and rate (FIG. 7B)
Figure 7B:
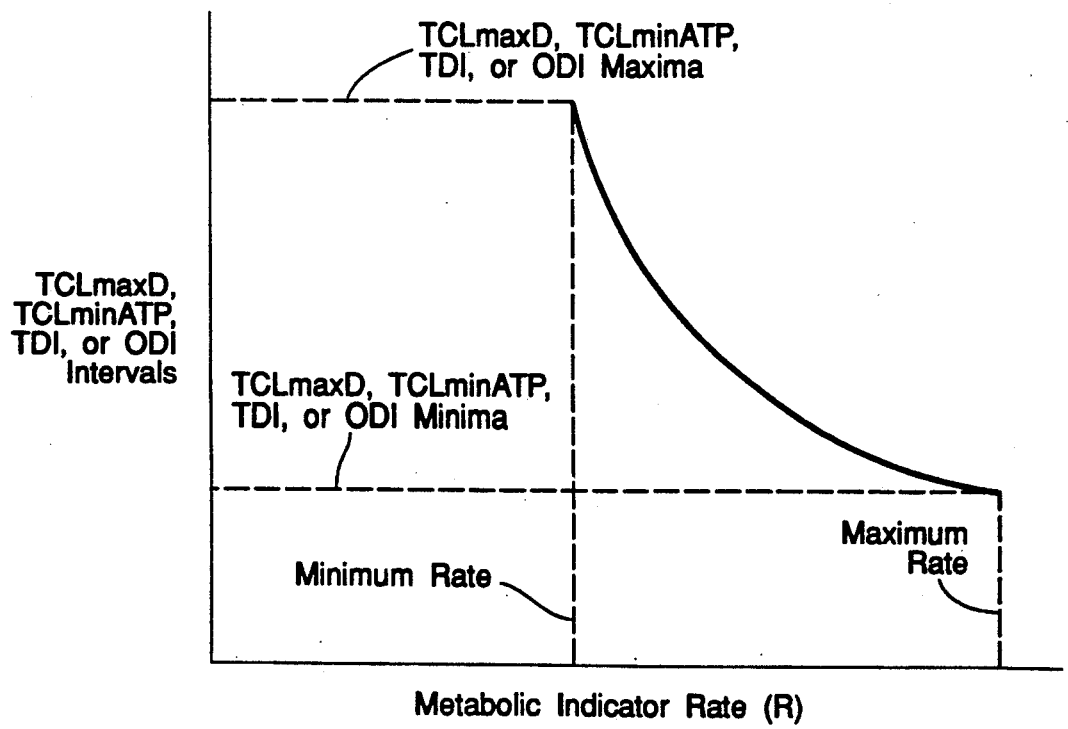

FIGS. 7A and 7B illustrate the manner of determining the TCLmaxD, TCLminATP, TDI and ODI from the metabolic indicator rate interval and metabolic indicator rate, respectively. The illustrative embodiment of the invention derives TCLmaxD, TCLminATP, TDI, and ODI for the current MIRI or MIR by linearly interpolating between two interval points. The method of determining TCLmaxD, TCLminATP and the TDI and ODI limits, illustrated by FIGS. 7A and 7B, is identical for each parameter. The upper interval limit in FIG. 7A is defined by the predetermined and preselected values of minimum rate interval, corresponding to maximum values of TCLmaxD, TCLminATP, TDI, and ODI. Maximum values of TCLmaxD, TCLminATP, TDI and ODI are independent and separate, although they may be preset to the same value. The lower interval limit in FIG. 7A is defined by the predetermined and preselected/ values of maximum rate interval, corresponding to minimum values of TCLmaxD, TCLminATP, TDL and ODI. Minimum values of TCLmaxD, TCLminATP, TDI and ODI are also independent and separate, although they may be preset to the same value. FIG. 7B illustrates the TCLmaxD, TCLminATP, TDI and ODI determination method in terms of MIR. (The end points for the TCLmaxD, TCLminATP, TDI and ODI curves may be programmable parameters, as will be understood by those skilled in the art.)

Figure 8A:
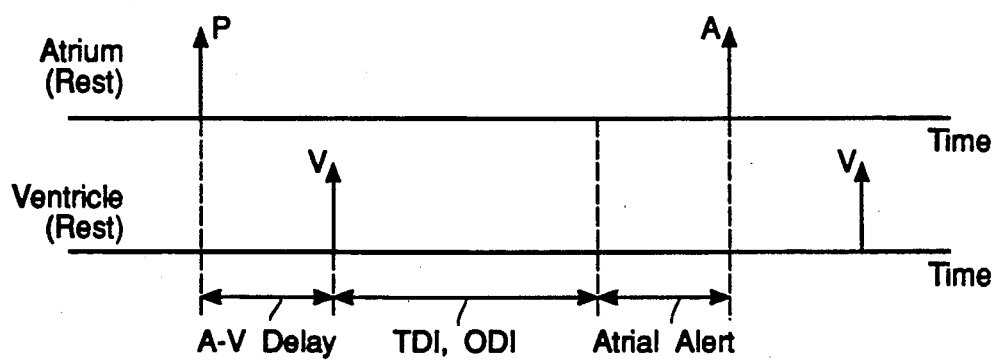
FIGS. 8A and 8B are timing diagrams of two cardiac cycles of different rates, and their associated timed intervals.
Figure 8B:
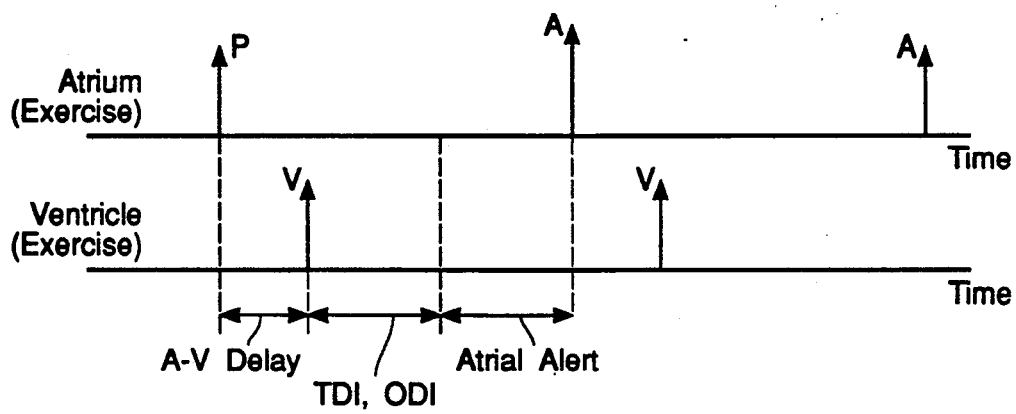

Referring to FIGS. 8A and 8B, timing diagrams of a cardiac cycle of a patient at rest (FIG. 8A) and an exercising patient (FIG. 8B) have there been illustrated. Following every ventricular beat V there is a time interval, encompassing the period from the beat V to the end of ODI or TDI, whichever is the longest, during which the pacer should not sense P waves. If the pacer generates a ventricular stimulus for a given pacing cycle, it blanks the atrial sense amplifier immediately after the pace to ignore atrial signals which are unreliable in the aftermath of a ventricular stimulus. Blanking normally lasts for about 80 ms. For the duration of the ODI and TDI (after the blanking period), the pacer enables atrial sensing. If the pacer senses a P wave during the TCLmax interval, the atria are beating too quickly. Because ODI and TDI encompass the interval immediately following the preceding A-V delay interval, any P wave occurring during this period is too close to the preceding atrial beat. The X/Y detector analyzes the history of P waves occurring during the ODI and TDI to determine whether to invoke antitachycardia pacing. By using the MIR to decrease the duration of ODI and TDI during exercise, as shown in FIG. 8B, the atrial beats which occur more rapidly as the sinus rhythm increases are now less likely to fall in ODI and TDI. Consequently, by having the metabolic indicator rate control these detection intervals, the MIR is able to extend the synchronous behavior of DDDR mode operation during periods of even heavy exercise.

The final interval in the pacing cycle shown in FIGS. 8A and 8B is the atrial alert period. The end of the atrial alert period, measured from the end of the last atrial cardiac cycle, corresponds to the minimum cardiac pacing rate which, in the illustrative embodiment of the invention, is the current value of the MIR. A P wave falling after the ODI and TDI intervals but before the end of the atrial alert period has a rate lower than the maximum atrial tracking rate. Such a P wave reflects a heart rate low enough to be considered non-pathological, so the pacer responds by triggering ventricular pacing in A-V synchrony (DDDR pacing), unless inhibited by an R wave. On the other hand, the pacer generates a stimulating pulse A in the atrium if it does not detect natural atrial activity before the end of the alert period; the A-V timing is also triggered in this case as well.

Figure 9:
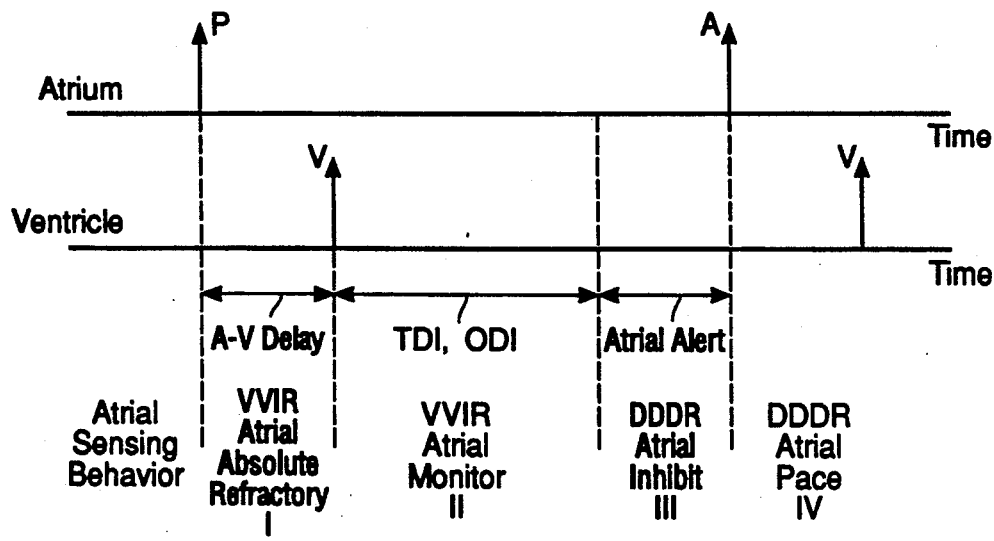
FIG. 9 is a timing diagram of a cardiac cycle and its associated timed intervals indicating how the pacemaker responds to a cardiac event when sensed in different timed intervals.
Figure 10A:
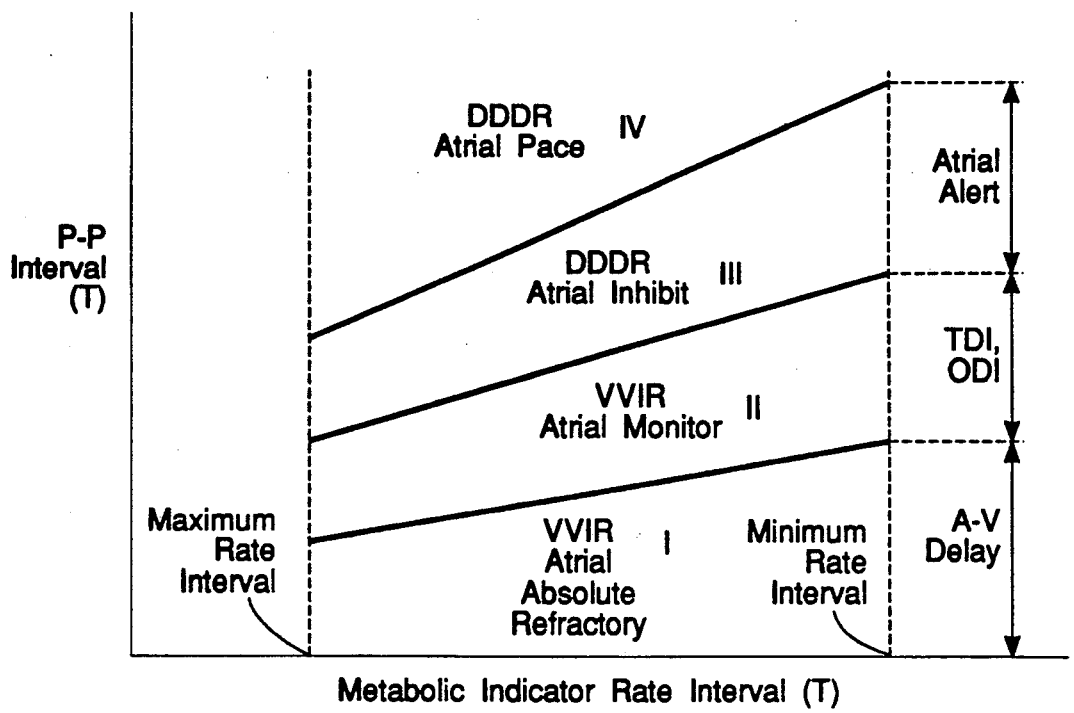
FIGS. 10A and 10B are graphs relating the rate of natural atrial sensing to the metabolic indicator rate parameter, in terms of cardiac cycle time and rate, respectively (the pacemaker bases the time boundaries for all intervals shown in FIGS. 6A to 7B on the metabolic indicator rate, while FIGS. 10A and 10B indicate how the pacemaker responds to a natural atrial depolarization as a function of metabolic indicator rate)
Figure 10B:
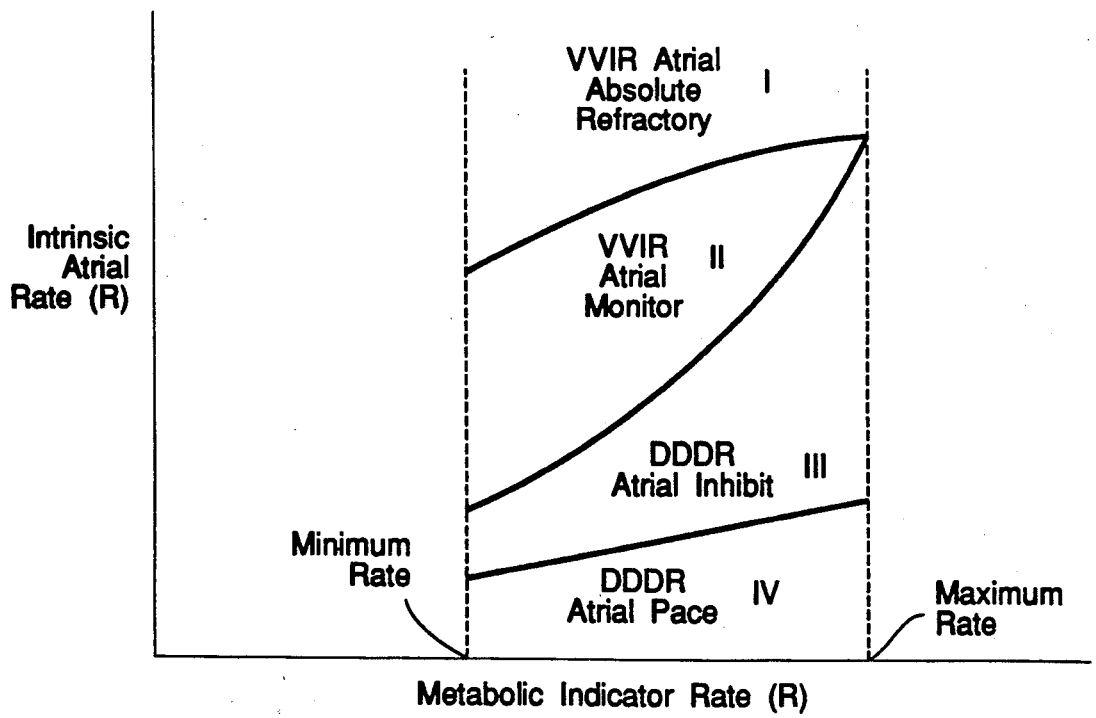

The timing diagram in FIG. 9 and the graphs of FIGS. 10A and 10B illustrate the manner of operation of the invention (FIG. 10B is derived from FIG. 10A simply by converting time values to the corresponding rates). When the MIR sets the maximum atrial tracking rate above the intrinsic atrial rate, sensed P waves will fall in the atrial alert interval and the effective pacing rate is under control of the sinus node. Operating in this manner, an atrial beat triggers the A-V delay, as in standard DDD pacing, but with the metabolic indicator rate automatically and continuously determining both the duration of the A-V delay and the cardiac cycle length. Pacing under these circumstances may be called the DDDR atrial inhibit mode because pacing is A-V synchronous with sensing inhibiting pacing in the ventricle and with the overall pacing rate determined by a metabolic (rate-responsive) sensor. This type of operation is represented by region III in FIGS. 9, 10A and 10B.

The MIR takes control only when the intrinsic atrial rate is too low or too high. If the intrinsic atrial rate is too low, causing time-out of the atrial alert timer as shown in FIG. 9, the pacer stimulates the atrium at the MIR and stimulates the ventricle after the A-V delay interval, as shown in region IV in FIGS. 9, 10A and 10B, unless natural ventricular activity inhibits pacing.

If the intrinsic atrial rate is faster than the maximum atrial tracking rate, the sinus rate is too high and the pacer senses during the ODI and TDI interval, as shown in region II of FIG. 9. Here, the pacer analyzes the history of the abnormal rhythm using the X/Y detector and, if it detects a VT condition, responds by invoking an antitachycardia therapy. (If the pacer senses a P wave in region I, during the A-V delay, it ignores it for all purposes.)

Figure 6A:
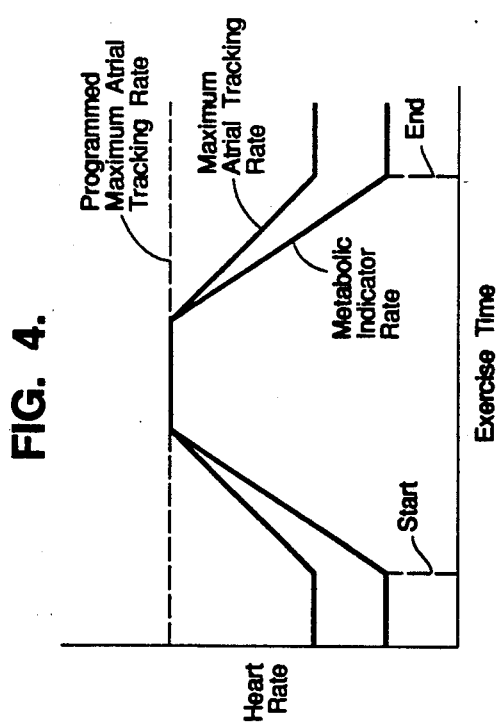
FIGS. 6A and 6B set forth graphic representations of the mechanism for automatically determining a rate-adaptable A-V delay interval from the metabolic indicator rate, in terms of cardiac cycle time (FIG. 6A) and rate (FIG. 6B)
Figure 6B:
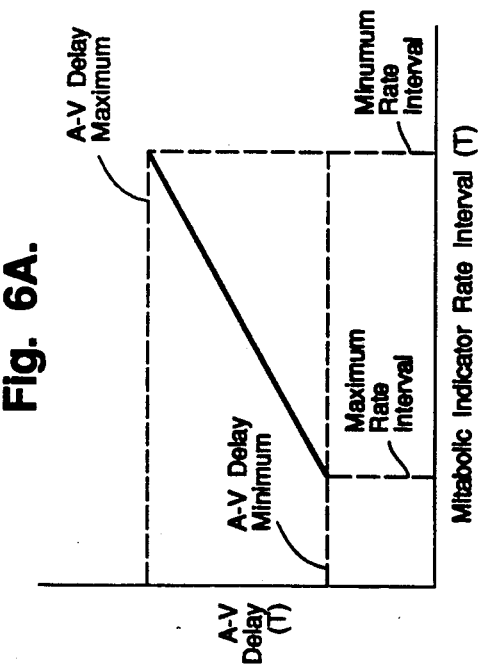

(d) The A-V delay is one of the parameters governing DDD pacing. At the end of the atrial cardiac cycle, upon time-out of the atrial alert timer or upon atrial sensing of an intrinsic atrial rate slower than the maximum atrial tracking rate, the pacemaker sets a timer to the A-V delay value. When the timer expires, unless pacing is inhibited by ventricular sensing prior to time-out, the pacemaker generates a stimulating pulse in the ventricle. The pacer varies the A-V delay interval in a manner inversely proportional to the MIR. FIGS. 6A and 6B illustrate the manner of determining the A-V delay from the metabolic indicator rate (MIR) or interval (MIRI). In the illustrative embodiment of the invention, the A-V delay for the current MIR or MIRI is determined by linearly interpolating between two points. In FIG. 6A, one point is defined by predetermined values of minimum rate interval and A-V delay maximum, the other by maximum rate interval and A-V delay minimum. FIG. 6B relates the A-V delay determination to MIR.

Referring to the cardiac cycle timing diagram in FIGS. 8A and 8B, the A-V delay interval becomes shorter in the presence of an exercise-induced acceleration of MIR. Changing the A-V delay inversely with respect to MIR promotes A-V synchrony when exercising. The pacer automatically shortens the A-V delay interval for faster metabolic indicator rates and increasing physiological intrinsic atrial rates.

Referring to FIG. 12, there is depicted in illustrative format one embodiment of an antitachycardia pacing algorithm according to the invention. A series of M (M=4) pacing trains (a pacing train is a series of pacing spikes controllably delivered in rapid succession) are delivered. For train 1, the initial A-V delay interval, derived from the MIR, is 10 ms. During a ventricular tachycardia, the atrium and the ventricle are often in dissociation; therefore it is preferable for the dual chamber antitachycardia pacing to begin with a very short A-V delay interval in order to re-establish association or synchrony as soon as possible between both chambers of the heart. The tachycardia cycle length (TCL) is 300 ms The V-A delay interval (the ventricular to atrial interval) is calculated as a programmable percentage of the TCL for the purpose of adapting to the varying cycle lengths of tachycardias, and has been programmed to seventy percent of the TCL (300 ms) in this embodiment, thereby establishing the calculated V-A delay interval as 210 ms. In this embodiment, the percentage of the TCL is taken as an average over the four previous sensed intervals, and remains fixed at this value (210 ms) during the course of the therapy For train 1, N=4, so that at the expiration of each of the 4 V-A delay intervals of 210 ms, an atrial pulse is delivered and at the expiration of each of the four A-V delay intervals of 10 ms a pulse is delivered to the ventricle, so that there are a total of N pairs of pulses (or 2N=8 pulses) delivered during train 1.

In train 2 of FIG. 12, the A-V delay interval has been programmed to increment in value from the low initial value of 10 ms in train 1 to the new value of 50 ms. The variation of the A-V delay interval is executed by computer software by standard methods known to those skilled in the art. In the same manner in trains 3 and 4 of FIG. 12, the A-V delay interval increases at the end of trains 2 and 3 to the increased values of 100 ms and 150 ms, respectively. In trains 2, 3, and 4, N=4, as in train 1, thereby delivering N (4) pairs of pacing pulses in each train. In this particular embodiment of the invention, the value of N is equal in all of the trains. However, N is a programmable parameter and may be programmed by the physician to suit the needs of a particular patient. Furthermore, N may have differing values for different trains in alternate embodiments of the invention.

As shown in FIG. 12, the A-V delay interval increments from 10 ms in train 1 to 150 ms in train 4. This parameter is also programmable and is patient dependent. The A-V delay may increment at the end of each train as in the preferred embodiment. However, the variation in the A-V delay is not necessarily limited to steady increments. It may include any combination of increases, plateaus and decreases in its value. Although it is preferable to include the variations at the end of each train, these may be executed at any time within a train and still fall within the scope of the invention.

Preferably, the initial value A-V delay interval is less than or equal to 60 ms.

The V-A delay interval in the preferred embodiment is programmed as a percentage of the TCL (70%). Although the invention does not limit the V-A delay interval to a particular range, it has been found that the best results occur when it lies within the range of thirty percent to one hundred percent of the TCL. Furthermore, its value is not necessarily fixed during the antitachycardia therapy, but may vary and still remain within the scope of the invention. If it is programmed to vary, the initial value is a percentage of the TCL; for example a percentage of the average cycle length of the last four intervals of the detected tachycardia. For instance, the V-A delay interval may include various combinations of increasing, decreasing, or remaining at a fixed value. Any programmed variations may occur at the end of trains or even within trains, or may even be a function of A-V delay interval variations.

In FIG. 12 the number of trains M is 4. The number of trains M is a patient dependent, physician programmable, parameter. At the completion of the M trains of antitachycardia pacing, the combined defibrillator pacing device returns to its normal operating mode, including the options of normal dual chamber (DDD) pacing or defibrillation shocks, if necessary. Furthermore, the device may provide bradycardia support pacing, if required, which may include either single chamber or dual chamber bradycardia support pacing.

Figure 13:
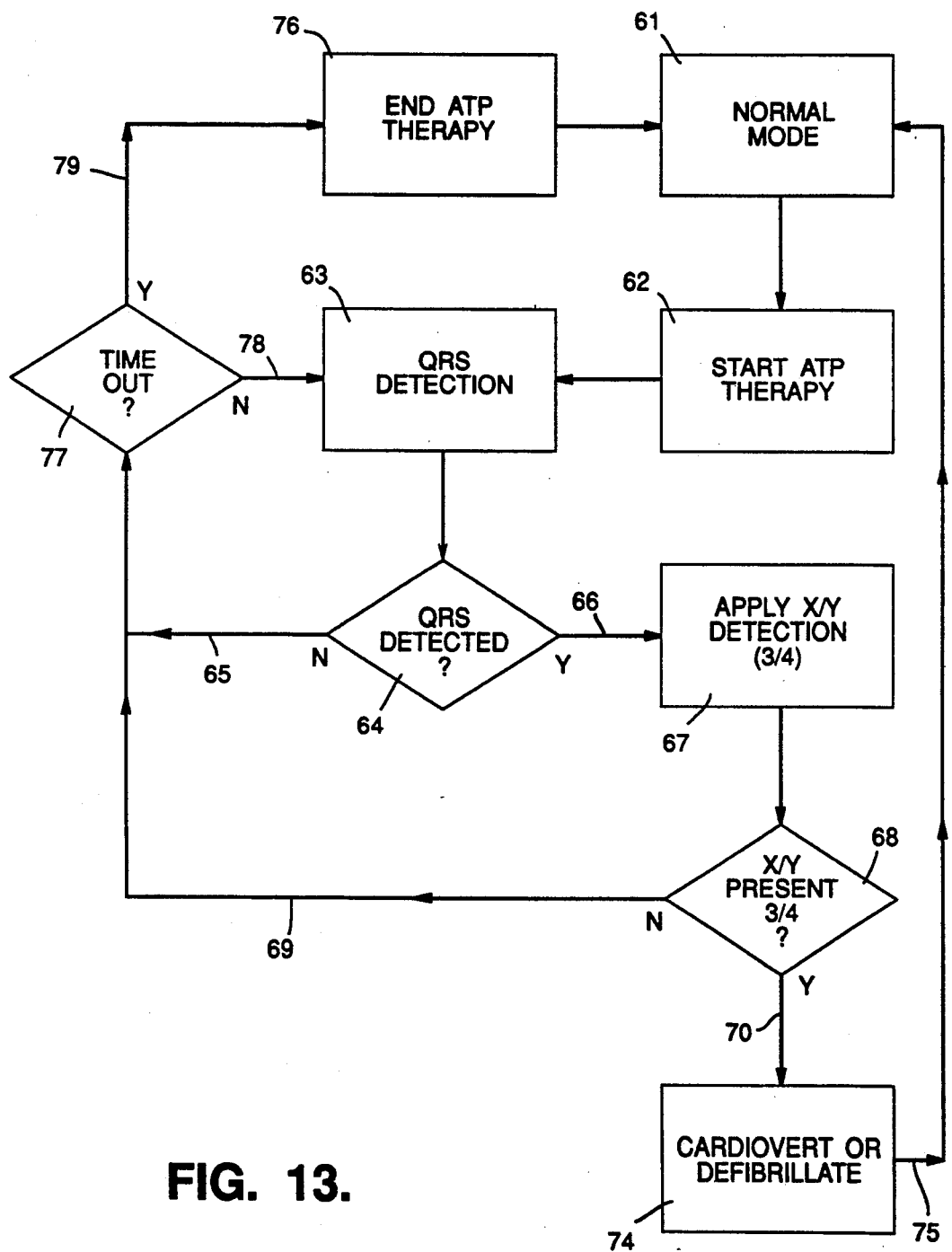
FIG. 13 is a flow chart for detection of acceleration to VF/fast VT during dual chamber antitachycardia pacing therapy.

FIG. 13 is a flowchart for the detection of acceleration to a VF or a fast VT during the application of the dual chamber antitachycardia pacing therapy. The normal operating mode is shown at block 61. Upon detection of tachycardia and its subsequent confirmation, dual chamber ATP therapy is applied at block 62. It is important, as a safety mechanism for the patient, during the application of any antitachycardia therapy, to prevent acceleration of VT to faster VT or to VF. QRS detection is switched on at block 63 during the ATP therapy to detect inherent QRS complexes which may occur either during the V-A interval or during the A-V delay. A decision is made at block 64 on the basis of whether or not QRS complexes are detected. If no QRS complexes are detected, control passes via 65 to timeout block 77. If time is out, i.e., if the programmed time for the dual chamber ATP therapy has expired, then control passes via 79 to the end of ATP therapy block 76, and normal operating mode is resumed at block 61. If at timeout block 77 the time has not expired, control passes via 78 to QRS detection block 63, and QRS detection is again commenced.

If there is detection of QRS complexes at block 64, control passes via 66 to apply X/Y detection block 67, where x/y detection is applied to determine whether the QRS complexes are regular or whether they are just isolated intrinsic beats. An example of x/y detection, in this embodiment, results when 3 beats out of 4 occur at intervals shorter than an acceleration detection window. The purpose of the acceleration detection window is to discern a condition of intensifying tachycardia rate. Programming of a parameter, delta, specifies the acceleration detection window by setting it to the detected tachycardia cycle length less delta (300 ms in the examples of FIG. 12). Delta is programmed as an absolute value or as percentage of the TCL. If delta is programmed to 75 ms, then 300 ms−75 ms=225 ms. Thus, the acceleration detection interval is considered sufficient to detect an acceleration of an existing tachycardia. The ¾ detection means that if any three out of the last four intervals are less than the acceleration detection window (225 ms), then the x/y detection criteria are satisfied.

At block 68, a decision is made to determine if the ¾ detection criterion applies to the QRS complexes. If the ¾ detection criterion is not met, control passes via 69 back to timeout block 77. If the time for therapy has not expired, control passes via 78 back to QRS detection block 63 and then either back to timeout block 77, if no QRS complexes are detected at this time, or back to the x/y detection block 67, if QRS complexes are detected.

If at block 68 the ¾ detection criterion has been met, control passes via 70 to block 74 which causes cardioversion or defibrillation therapy to be applied. It has been found safer and more effective to use the foregoing acceleration detection, combined with cardioversion or defibrillation therapy as shown in FIG. 13, than to wait until the end of ATP therapy and face the possibility of a degeneration to a very fast VT or a VF. After cardioversion or defibrillation therapy at block 74, the device returns control via 75 to its normal mode of operation block 61.

Although the invention has been described with reference to a particular embodiment, it is to be understood that this embodiment is merely illustrative of the application of the principles of the invention. Hence numerous modifications may be made therein and other arrangements may be devised without departing from the spirit and scope of the invention. For example, the described embodiment includes a control mechanism described as a microprocessor which may be replaced by any control circuitry capable of performing the same functions and operations.

What is claimed is:

1. A dual chamber antitachycardia pacing device for the reversion of tachycardias in a patient's heart, comprising:
   means for generating atrial and ventricular stimulation pulses,
   means for determining the patient's intrinsic atrial heartbeat rate,
   at least one means for determining the patient's metabolic indicator rate,
   means for determining the patient's maximum atrial tracking rate as a function of said metabolic indicator rate,
   means for comparing said intrinsic atrial heartbeat rate to said maximum atrial tracking rate, and
   means responsive to said comparing means for controlling said generating means to operate in a first mode in which ventricular pacing pulses are generated in synchrony with said intrinsic atrial heartbeat rate when said intrinsic atrial heartbeat rate is slower than said maximum atrial tracking rate, and for controlling said generating means to operate in a second, antitachycardia pacing, mode when said intrinsic atrial heartbeat rate exceeds said maximum atrial tracking rate.

2. A dual chamber antitachycardia pacing device according to claim 1, wherein said stimulation pulse generating means, when operating in synchrony with said intrinsic atrial heartbeat rate and in the absence of an intrinsic ventricular heartbeat, generates a ventricular pulse after an A-V delay interval following each intrinsic atrial heartbeat, and further including means for adjusting said A-V delay interval as a function of said metabolic indicator rate.

3. A dual chamber antitachycardia pacing device for the reversion of tachycardias in a patient's heart, comprising:

means for generating atrial and ventricular stimulation pulses, means for determining the patient's intrinsic atrial heartbeat rate, at least one means for determining the patient's metabolic indicator rate, means for determining the patient's maximum atrial tracking rate as a function of said metabolic indicator rate, means for comparing said intrinsic atrial heartbeat rate to said maximum atrial tracking rate, and means responsive to said comparing means for controlling said generating means to operate in a first mode in which ventricular pacing pulses are generated in synchrony with said intrinsic atrial heartbeat rate when said intrinsic atrial heartbeat rate is slower than said maximum atrial tracking rate, and for controlling said generating means to operate in a second, antitachycardia pacing, mode when said intrinsic atrial heartbeat rate exceeds said maximum atrial tracking rate, wherein in said second mode, atrial and ventricular pacing pulses are generated and delivered in a series of pulse trains with each train consisting of a plurality of pacing pulses delivered in an alternating pulse sequence to the ventricle and to the atrium.

4. A dual chamber antitachycardia pacing device according to claim 3, wherein said stimulation pulse generating means, when operating in said second mode, delivers said alternating pulse sequence so that timing of said delivered pulses is in accordance with the value of the A-V interval, whereby each train comprises the delivery of a pacing pulse to the atrium at the expiration of each V-A delay interval and a pacing pulse to the ventricle at the expiration of each A-V delay interval, and means for varying said A-V delay interval from an initial value, which is determined as a function of said metabolic indicator rate, and is adjusted at least once prior to completion of each of said series of pulse trains.

5. A dual chamber antitachycardia pacing device according to claim 2, wherein said at least one means for determining the patient's metabolic indicator rate includes a fast-acting sensor means for deriving a rapidly varying metabolic indicator rate and a slower-acting sensor means for deriving a slowly varying, stabilized, metabolic indicator rate, and wherein said metabolic indicator rate is determined to be the faster one of the two metabolic indicator rates derived by said fast-acting sensor means and said slower-acting sensor means.

6. A dual chamber antitachycardia pacing device according to claim 5 wherein said fast-acting sensor means derives intracardia evoked potential amplitude and said slower-acting sensor means derives respiratory minute volume.

7. A dual chamber antitachycardia pacing device for the reversion of tachycardias in a patient's heart, comprising:

means for generating atrial and ventricular stimulation pulses, means for determining the patient's intrinsic atrial heartbeat rate, at least one means for determining the patient's metabolic indicator rate, means for comparing said metabolic indicator rate with said intrinsic atrial heartbeat rate and, depending on the results of the comparison, classifying said intrinsic atrial heartbeat rate as either physiological or pathological; and control means operative when the atrial heartbeat rate is physiological for controlling said stimulation pulse generating means to operate in response to said intrinsic atrial heartbeat rate, and operative when the atrial heartbeat rate is pathological for controlling said stimulation pulse generating means to operate in an antitachycardia pacing mode.

8. A dual chamber antitachycardia pacing device according to claim 7, wherein said stimulation pulse generating means, when operating in synchrony with said intrinsic atrial heartbeat rate and in the absence of an intrinsic ventricular heartbeat, generates a ventricular pulse after an A-V delay interval following each intrinsic atrial heartbeat, and further including means for adjusting said A-V delay interval as a function of said metabolic indicator rate.

9. A dual chamber antitachycardia pacing device for the reversion of tachycardias in a patient's heart, comprising:

means for generating atrial and ventricular stimulation pulses, means for determining the patient's intrinsic atrial heartbeat rate, at least one means for determining the patient's metabolic indicator rate, means for comparing said metabolic indicator rate with said intrinsic atrial heartbeat rate and, depending on the result of the comparison, classifying said intrinsic atrial heartbeat rate as either physiological or pathological; and control means operative when the atrial heartbeat rate is physiological for controlling said stimulation pulse generating means to operate in response to said intrinsic atrial heartbeat rate, and operative when the atrial heartbeat rate is pathological for controlling said stimulation pulse generating means to operate in an antitachycardia pacing mode, wherein in said antitachycardia pacing mode, atrial and ventricular pacing pulses are generated and delivered in a series of pulse trains with each train consisting of a plurality of pacing pulses delivered in an alternating pulse sequence to the ventricle and to the atrium.

10. A dual chamber antitachycardia pacing device according to claim 9 wherein said stimulation pulse generating means, when operating in said antitachycardia pacing mode, delivers said alternating pulse sequence so that timing of said delivered pulses is in accordance with the value of the A-V interval, whereby each train comprises the delivery of a pacing pulse to the atrium at the expiration of each V-A delay interval and a pacing pulse to the ventricle at the expiration of each A-V delay interval, and means for varying said A-V delay interval from an initial value, which is determined as a function of said metabolic indicator rate and is adjusted at least once prior to completion of each of said series of pulse trains.

11. A dual chamber antitachycardia pacing device according to claim 9 wherein said at least one means for determining the patient's metabolic indicator rate includes a fast-acting sensor means for deriving a rapidly varying metabolic indicator rate and a slower-acting sensor means for deriving a slowly varying, stabilized, metabolic indicator rate, and wherein said metabolic indicator rate is determined to be the faster one of the two metabolic indicator rates derived by said fast-acting sensor means and said slower-acting sensor means.

12. A dual chamber antitachycardia pacing device according to claim 11 wherein said fast-acting sensor means derives intracardiac evoked potential amplitude and said slower-acting sensor means derives respiratory minute volume.

13. A dual chamber antitachycardia pacing device for the reversion of tachycardias in a patient's heart, comprising:
   means for generating atrial and ventricular pacing pulses;
   means for sensing atrial and ventricular heartbeats;
   at least one means for determining a metabolic indicator rate;
   means for ascertaining whether sensed atrial heartbeats are occurring at a rate which is pathological for said metabolic indicator rate; and
   means for controlling said generating and sensing means to operate normally in a DDDR mode but to switch to an antitachycardia pacing mode when the rate of the atrial heartbeats is pathological.

14. A dual chamber antitachycardia pacing device according to claim 13, wherein said pacing pulse generating means, when operating in synchrony with intrinsic atrial heartbeats and in the absence of intrinsic ventricular heartbeats, generates a ventricular pulse after an A-V delay interval following each intrinsic atrial heartbeat, and further including means for adjusting said A-V delay interval as a function of said metabolic indicator rate.

15. A dual chamber antitachycardia pacing device according to claim 13, wherein said at least one means for determining a metabolic indicator rate includes a fast-acting sensor means for deriving a rapidly varying metabolic indicator rate and a slower-acting sensor means for deriving a slowly varying, stabilized, metabolic indicator rate, and wherein said metabolic indicator rate is determined to be the faster one of the two metabolic indicator rates derived by said fast-acting sensor means and said slower-acting sensor means.

16. A dual chamber antitachycardia pacing device according to claim 15, wherein said fast-acting sensor means derives intracardiac evoked potential amplitude and said slower-acting sensor means derives respiratory minute volume.

17. A dual chamber antitachycardia pacing device for the reversion of tachycardias in a patient's heart, comprising:
   means for generating atrial and ventricular pacing pulses;
   means for sensing atrial and ventricular heartbeats;
   at least one means for determining a metabolic indicator rate;
   means for ascertaining whether sensed atrial heartbeats are occurring at a rate which is pathological for said metabolic indicator rate; and
   means for controlling said generating and sensing means to operate normally in a DDDR mode but to switch to an antitachycardia pacing mode when the rate of the atrial heartbeats is pathological,
   wherein in said antitachycardia pacing mode, atrial and ventricular pacing pulses are generated and delivered in a series of pulse trains with each train consisting of a plurality of pacing pulses delivered in an alternating pulse sequence to the ventricle and to the atrium.

18. A dual chamber antitachycardia pacing device according to claim 17, wherein said pacing pulse generating means, when operating in said antitachycardia pacing mode, delivers said alternating pulse sequence so that timing of said delivered pulses is in accordance with the value of the A-V interval, whereby each train comprises the delivery of a pacing pulse to the atrium at the expiration of each V-A delay interval and a pacing pulse to the ventricle at the expiration of each A-V delay interval, and means for varying said A-V delay interval from an initial value, which is determined as a function of said metabolic indicator rate and is adjusted at least once prior to completion of each of said series of pulse trains.

19. A method of utilizing a dual chamber antitachycardia pacing device to revert tachycardias in a patient's heart, comprising the steps of:
   determining the patient's intrinsic atrial heartbeat rate,
   determining the patient's metabolic indicator rate,
   determining a maximum atrial tracking rate as a function of said metabolic indicator rate,
   comparing said intrinsic atrial heartbeat rate to said maximum atrial tracking rate, and
   in response to said comparing step, generating ventricular pacing pulses in synchrony with said atrial heartbeat rate when said intrinsic atrial heartbeat rate is slower than said maximum atrial tracking rate and generating pacing pulses in an antitachycardia therapy mode when said intrinsic atrial heartbeat rate exceeds said maximum atrial tracking rate.

20. A method according to claim 19, wherein during said step of generating ventricular pacing pulses, when ventricular pacing pulses are being generated in synchrony with said intrinsic atrial heartbeat rate, each of said ventricular pulses is generated after an A-V delay interval which follows an atrial heartbeat, said method further including the step of adjusting said A-V delay interval as a function of said metabolic indicator rate.

21. A method of utilizing a dual chamber antitachycardia pacing device to revert tachycardias in a patient's heart, comprising the steps of:
   determining the patient's intrinsic atrial heartbeat rate,
   determining the patient's metabolic indicator rate,
   determining a maximum atrial tracking rate as a function of said metabolic indicator rate,
   comparing said intrinsic atrial heartbeat rate to said maximum atrial tracking rate, and
   in response to said comparing step, generating ventricular pacing pulses in synchrony with said atrial heartbeat rate when said intrinsic atrial heartbeat rate is slower than said maximum atrial tracking rate and generating pacing pulses in an antitachycardia therapy mode when said intrinsic atrial heartbeat rate exceeds said maximum atrial tracking rate,
   wherein said antitachycardia therapy mode includes the sub-steps of:
   delivering a pulse to the ventricle,
   determining a V-A delay interval as a function of said metabolic indicator rate,
   delivering a pulse to the atrium at the expiration of said determined V-A interval in the absence of an intrinsic atrial heartbeat during said V-A interval,
   determining an A-V delay interval as a function of said metabolic indicator rate, delivering a pulse to the ventricle at the expiration of said A-V interval in the absence of an intrinsic ventricular heartbeat during said A-V interval, repeating the aforesaid pulse deliveries to the atrium and the ventricle for a plurality of intervals defining a pulse train, and varying said A-V delay interval value from the initial value at least once prior to the completion of a series of trains of pulses.

22. A method according to claim 20, wherein said step of determining the patient's metabolic indicator rate includes the sub-steps of:

deriving a first, rapidly varying, metabolic indicator rate, deriving a second, slowly varying, stable metabolic indicator rate, and determining the metabolic indicator rate to be the faster one of said first and second metabolic indicator rates.

23. A method according to claim 22, wherein said first metabolic indicator rate comprises a function of the patient's intracardiac evoked potential amplitude and said second metabolic indicator rate comprises a function of the patient's respiratory minute volume.

24. A method of utilizing a dual chamber antitachycardia pacing device to revert tachycardias in a patient's heart, comprising the steps of generating atrial and ventricular pacing pulses;

sensing the patient's atrial and ventricular heartbeats and determining the patient's atrial and ventricular heartbeat rates;

determining the patient's metabolic indicator rate;

ascertaining whether sensed atrial heartbeats are occurring at a rate which is pathological for said metabolic indicator rate; and performing said generating and sensing steps in a DDDR mode when said atrial heartbeat rate is non-pathological, and in an antitachycardia pacing mode when said atrial heartbeat rate is pathological.

25. A method according to claim 24, wherein during said step of generating ventricular pacing pulses, when ventricular pacing pulses are being generated in synchrony with said intrinsic atrial heartbeat rate, each of said ventricular pulses is generated after an A-V delay interval which follows an atrial heartbeat, said method further including the step of adjusting said A-V delay interval as a function of said metabolic indicator rate.

26. A method of utilizing a dual chamber antitachycardia pacing device to revert tachycardias in a patient's heart, comprising the steps of:

generating atrial and ventricular pacing pulses;

sensing the patient's atrial and ventricular heartbeats and determining the patient's atrial and ventricular heartbeat rates;

determining the patient's metabolic indicator rate;

ascertaining whether sensed atrial heartbeats are occurring at a rate which is pathological for said metabolic indicator ate; and performing said generating and sensing steps in a DDDR mode when said atrial heartbeat rate is non-pathological, and in an antitachycardia pacing mode when said atrial heartbeat rate is pathological, wherein said antitachycardia therapy mode includes the substeps of:

delivering a pulse to the ventricle, determining a V-A delay interval as a function of said metabolic indicator rate, delivering a pulse to the atrium at the expiration of said determined V-A interval in the absence of an intrinsic atrial heartbeat during said V-A interval, determining an A-V delay interval as a function of said metabolic indicator rate, delivering a pulse to the ventricle at the expiration of said A-V interval in the absence of an intrinsic ventricular heartbeat during said A-V interval, repeating the aforesaid pulse deliveries to the atrium and the ventricle for a plurality of intervals defining a pulse train, and varying said A-V delay interval value from the initial value at least once prior to the completion of a series of trains of pulses.

27. A method according to claim 26, wherein said step of determining the patient's metabolic indicator rate includes the sub-steps of:

deriving a first, rapidly varying metabolic indicator rate, deriving a second, slowly varying, stable, metabolic indicator rate, and determining the metabolic indicator rate to be the faster one of said first and second metabolic indicator rates.

28. A method according to claim 27, wherein said first metabolic indicator rate comprises a function of the patient's intracardiac evoked potential amplitude and said second metabolic indicator rate comprises a function of the patient's respiratory minute volume.

* * * * *